US011006986B2

(12) United States Patent
Venturini et al.

(10) Patent No.: US 11,006,986 B2
(45) Date of Patent: May 18, 2021

(54) INTERNAL FIXATION DEVICE FOR THE PEDIATRIC CORRECTION OF SEVERE BONE MALFORMATIONS

(71) Applicant: ORTHOFIX S.R.L., Bussolengo (IT)

(72) Inventors: Daniele Venturini, Povegliano Veronese (IT); Marco Magni, Ferrara (IT); Andrea Zaccaria, Tregnago (IT)

(73) Assignee: ORTHOFIX S.R.L., Bussolengo (IT)

( * ) Notice: Subject to any disclaimer, the term of this patent is extended or adjusted under 35 U.S.C. 154(b) by 345 days.

(21) Appl. No.: 16/094,099

(22) PCT Filed: Apr. 14, 2017

(86) PCT No.: PCT/EP2017/059048
§ 371 (c)(1),
(2) Date: Oct. 16, 2018

(87) PCT Pub. No.: WO2017/178642
PCT Pub. Date: Oct. 19, 2017

(65) Prior Publication Data
US 2019/0110822 A1 Apr. 18, 2019

(30) Foreign Application Priority Data

Apr. 15, 2016 (IT) .................. 102016000039009

(51) Int. Cl.
*A61B 17/74* (2006.01)
*A61B 17/80* (2006.01)
(Continued)

(52) U.S. Cl.
CPC .......... *A61B 17/748* (2013.01); *A61B 17/746* (2013.01); *A61B 17/8057* (2013.01);
(Continued)

(58) Field of Classification Search
CPC . A61B 17/746; A61B 17/748; A61B 17/8057; A61B 17/8605; A61B 17/863;
(Continued)

(56) References Cited

U.S. PATENT DOCUMENTS 5,002,544 A * 3/1991 Klaue ................... A61B 17/80
606/280
2004/0102776 A1* 5/2004 Huebner ............ A61B 17/8052
606/281
(Continued)

FOREIGN PATENT DOCUMENTS

JP    2003024344    1/2003
JP    2004216056    8/2004
(Continued)

OTHER PUBLICATIONS

European Patent Office, "Search Report" In application No. PCT/EP2017/059048, dated Aug. 1, 2017, 4 pages.

*Primary Examiner* — Jessica Weiss
(74) *Attorney, Agent, or Firm* — Hickman Becker Bingham Ledesma LLP; Malgorzata A. Kulczycka

(57) ABSTRACT

The invention concerns an inner plate fixator device (1) for the correction of severe bone malformations, of the type comprising an elongated plate (2, 2') in which through holes (3, 4) for receiving bone screws are provided.

The use of this fixator device allows the pediatric correction of severe bone malformations, in particular malformations of the proximal portion of the femur.

10 Claims, 26 Drawing Sheets

(51) Int. Cl.
  *A61B 17/00* (2006.01)
  *A61B 17/86* (2006.01)
(52) U.S. Cl.
  CPC ........... *A61B 17/863* (2013.01); *A61B 17/864* (2013.01); *A61B 17/8605* (2013.01); *A61B 2017/00477* (2013.01)
(58) Field of Classification Search
  CPC .............. A61B 17/864; A61B 17/8023; A61B 17/8061; A61B 2017/00477
  USPC ...................................... 606/70–71, 280–299
  See application file for complete search history.

(56) References Cited

U.S. PATENT DOCUMENTS

| | | | |
|---|---|---|---|
| 2004/0102778 A1* | 5/2004 | Huebner | A61B 17/8033 606/71 |
| 2006/0089648 A1 | 4/2006 | Masini | |
| 2006/0149252 A1* | 7/2006 | Markworth | A61B 17/7037 606/900 |
| 2009/0012569 A1* | 1/2009 | Dall | A61B 17/748 606/280 |
| 2011/0218534 A1* | 9/2011 | Prandi | A61B 17/80 606/71 |
| 2015/0173812 A1* | 6/2015 | Masson | A61B 17/80 606/70 |
| 2016/0000481 A1* | 1/2016 | Ehmke | A61B 17/8863 606/71 |
| 2016/0000482 A1* | 1/2016 | Ehmke | A61B 17/8863 606/71 |
| 2016/0066968 A1* | 3/2016 | Orsak | A61B 17/74 606/71 |

FOREIGN PATENT DOCUMENTS

| | | | | |
|---|---|---|---|---|
| WO | WO 2005/094707 A2 | 10/2005 | | |
| WO | WO 2006/097729 A1 | 9/2006 | | |
| WO | WO-2006097729 A1 * | 9/2006 | ......... | A61B 17/8085 |

* cited by examiner

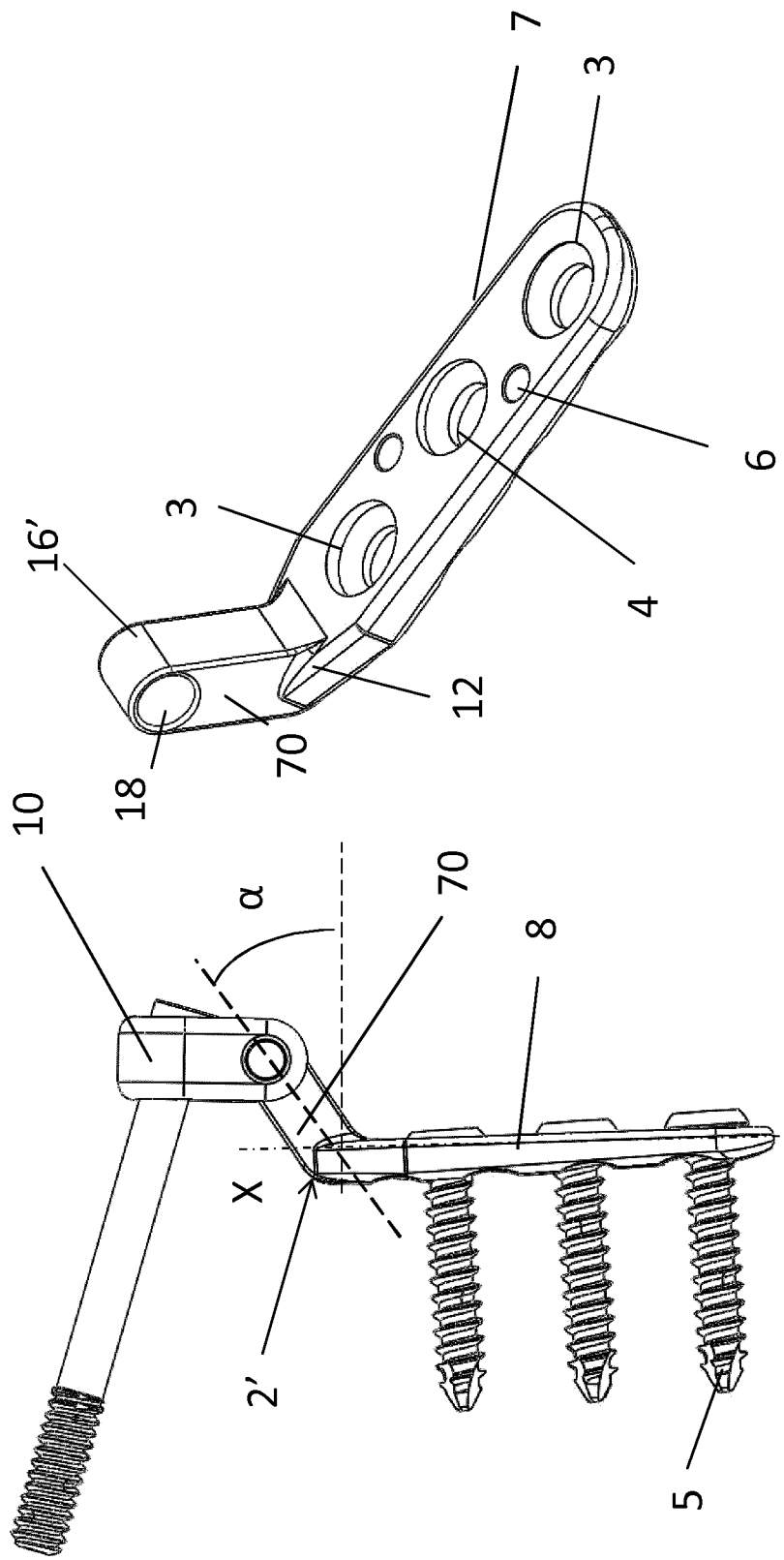

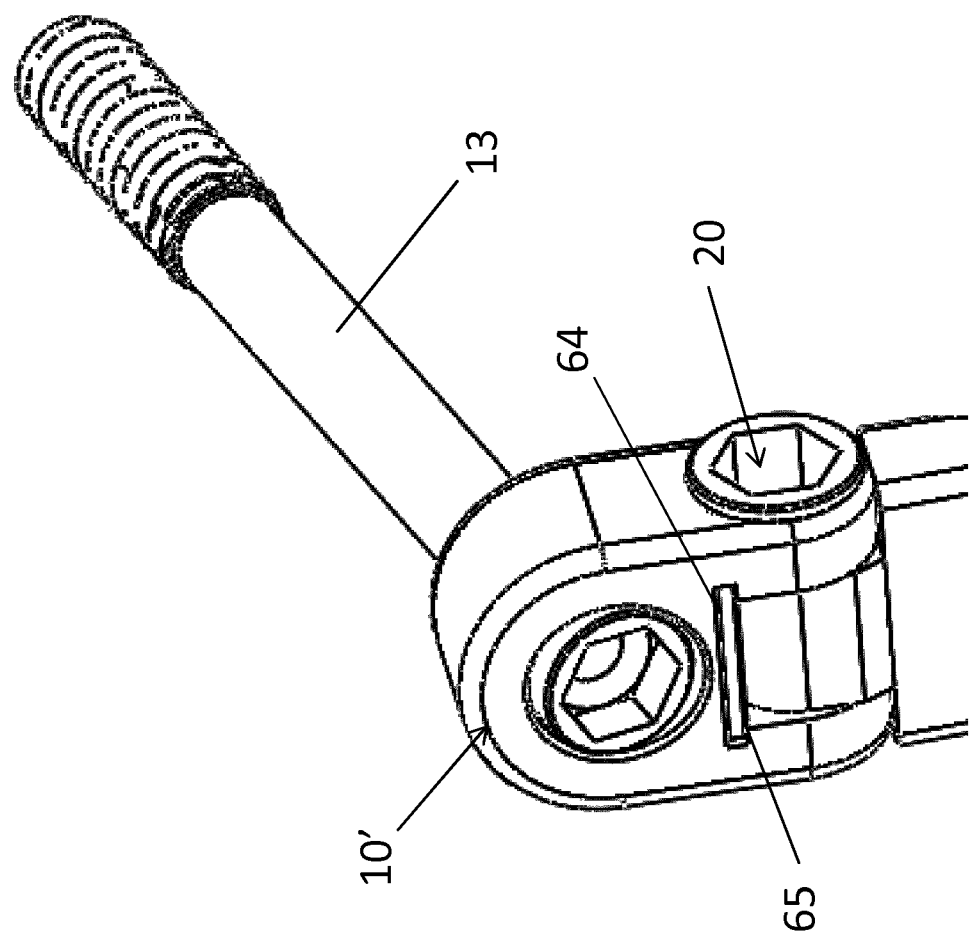

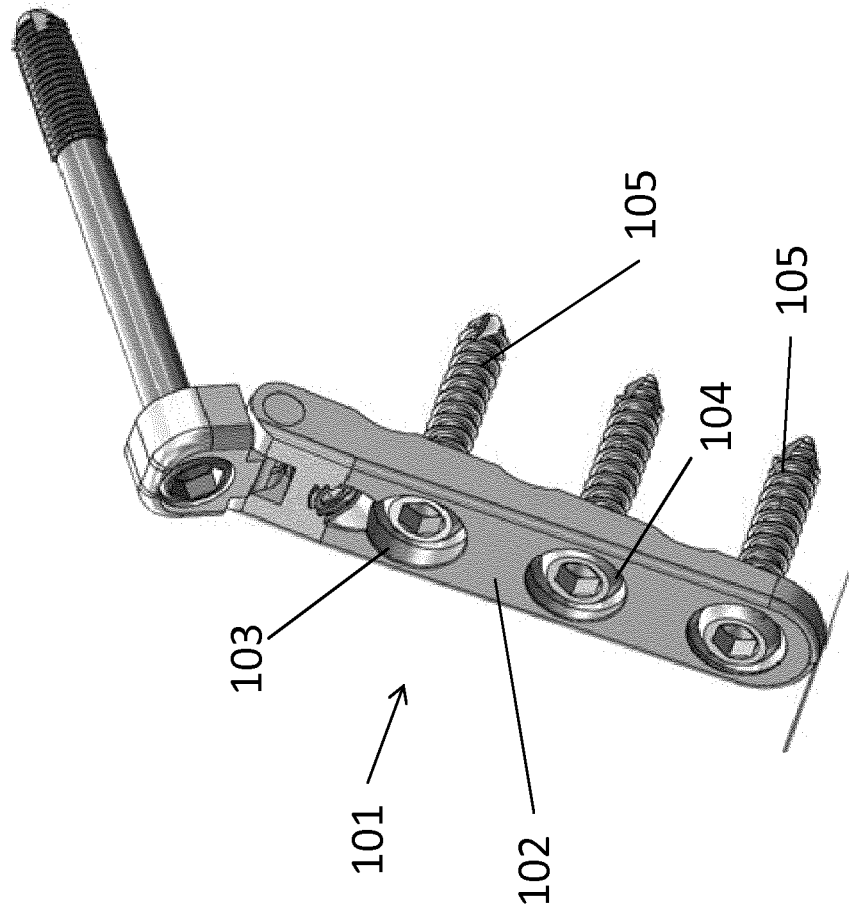

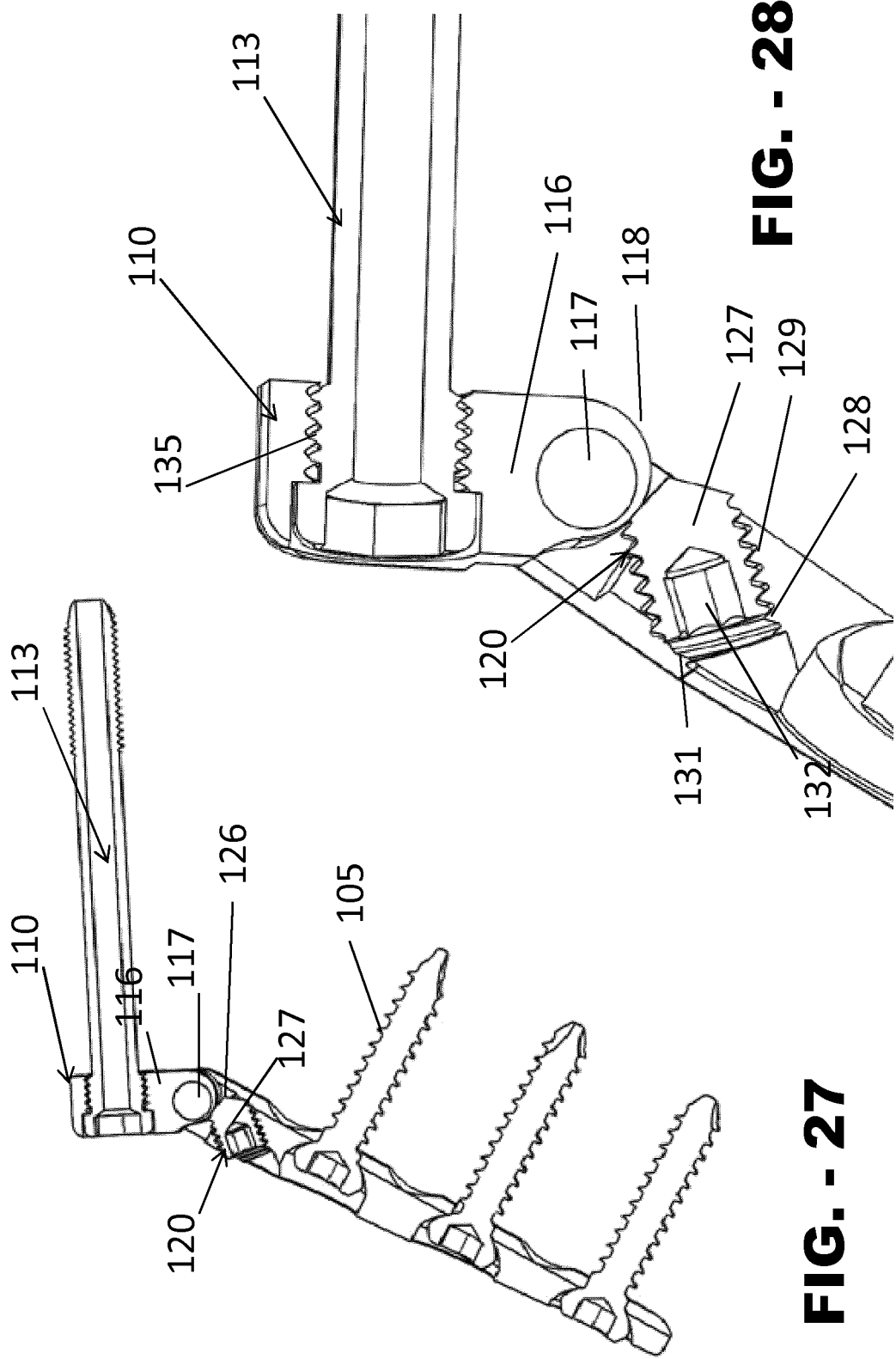

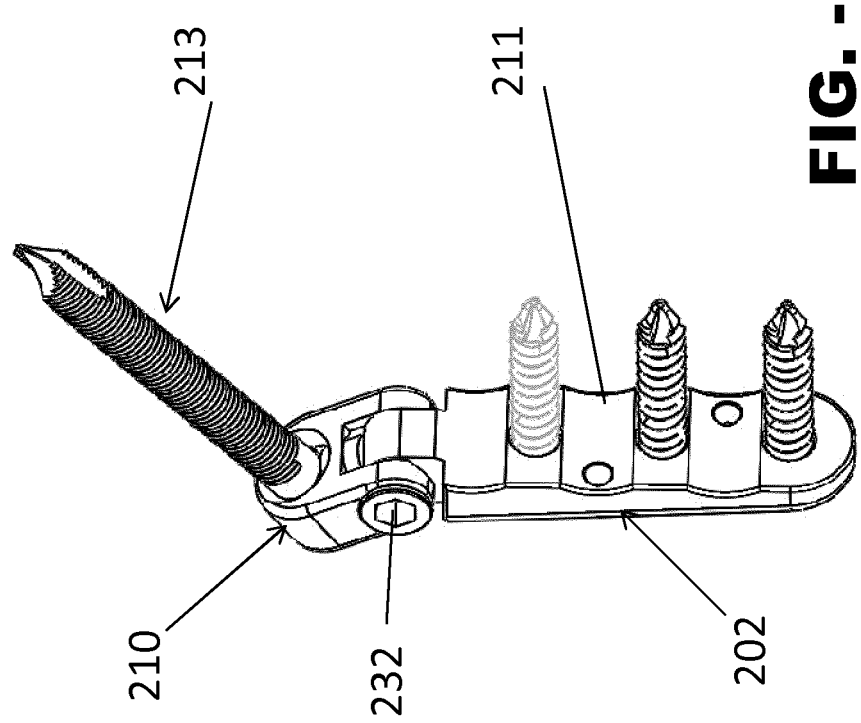

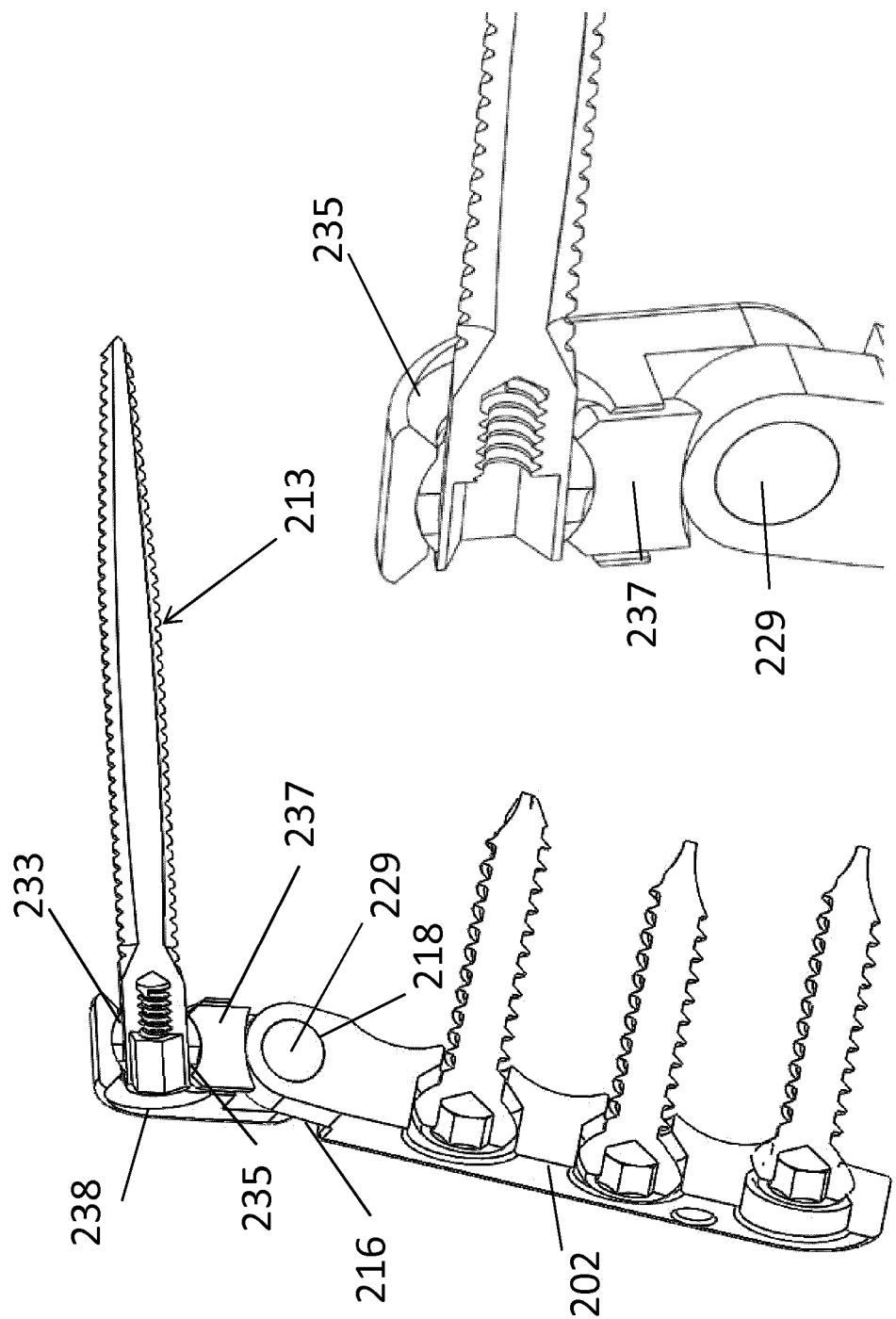

INTERNAL FIXATION DEVICE FOR THE PEDIATRIC CORRECTION OF SEVERE BONE MALFORMATIONS

BENEFIT CLAIM

This application claims the benefit of and is a national stage entry under 35 U.S.C. § 371 from PCT international application PCT/EP2017/059048, filed 14 Apr. 2017, which claims the benefit of Italy patent application 102016000039009, filed 15 Apr. 2016, the entire contents of which are hereby incorporated by reference as if fully set forth herein.

DESCRIPTION

The present invention concerns an inner plate fixator device for the pediatric correction of severe bone malformations, of the type comprising an elongated plate in which through holes for receiving bone screws are provided.

In particular, the invention concerns, without limitation, an inner plate fixator device intended to be used in pediatric reconstruction to solve severe malformations of the proximal portion of the femur, such as the lack of the femoral head or the need to translate the anatomical axis to allow a correct load axis and the hereinafter disclosure relates to this field of application with the only purpose to ease its explanation.

FIELD OF APPLICATION

In the specific sector of the present invention some problems are known which afflict the proximal portion of the femur and which are caused by inborn malformations.

For example, there are severe malformations wherein the femoral head is completely absent or positioned in an inappropriate anatomic position. In other cases, the presence of a pseudoarthrosis of the femoral neck changes the natural formation and conformation of the femoral head.

In still more severe cases, the femur is absent or there is a shortened femur and the angle between the femoral axis and the femoral neck is not correct.

These problems often occur with bilateral frequency; however, in some cases they can afflict only one of the two lower limbs.

These malformations are considered due to defects in the primary ossification centre or to cartilage diseases.

The malformations we are dealing with result in a severe and apparent shortening of one or of both legs. Moreover, the shortening percentage remains constant with growth. The thigh remains short, often flexed, and rotated outwardly, though the feet conformation may appear normal.

Only operations from a very young age, for example from two or three years of age of the patient, may enable to partially remedy these severe inborn malformations.

PRIOR ART

One solution presently adopted by the prior art consists in stabilizing the femur head into the correct position thus managing the bone growth into the desired position. Thereby, the stability in the femur trochanteric region is also encouraged.

Such an option implies a surgical operation to be performed during the pediatric age with implantation of a femoral plate equipped with one or two cephalic screws which has an end fixed to the plate and the opposite end that penetrates into the femoral trochanteric portion.

The operation must be performed during the pediatric age taking care of stabilizing the femoral head into the correct position thus managing the bone growth into the desired position and encouraging at the same time the trochanteric area stability.

However, even though this is the only solution presently suggested by the art, other collateral problems can be found especially during the patient's developmental age from 2 to ten years old.

First of all, there are serious problems in the implanting step of the plate due to the size of what the femoral neck will have to be; indeed, during childhood, the bone portion where the screw is inserted may have very small dimensions, of even just 5 mm diameters.

Another huge problem is due to the difficulty in selecting the exact angle and position of the femoral neck, despite the use of X-rays or ultrasound imaging means.

In the here enclosed FIG. 1, an X-ray image of a femoral plate of the known type implanted in the proximal portion of a femur suffering from an inborn malformation is shown. As it can be noticed from this image, the plate has an extended fixed angle cephalic screw that, unfortunately, does not find the femoral neck, with all the resulting drawbacks.

It must also be said that the dimensions of the cephalic screw are not anatomically appropriate with the dimensions of the femoral neck in this case.

A known solution is disclosed in the International patent application No. WO 2006/097729 wherein a femoral plate is disclosed with a proximal portion hinged to a distal portion and including locking means for locking the relative angular positioning of the two portions. However, this solution is not for the use with a cephalic screw but with few bone screws 124 inserted in corresponding screw holes.

Another solution is disclosed in the French patent No. FR 2 271 800 wherein a femoral plate is disclosed with a proximal portion for a couple of cephalic screws and hinged to a distal portion; however, this solution does not include locking means for locking the relative angular positioning of the two portions.

The technical problem underlying the present invention is devising an inner plate fixator device for the pediatric correction of severe bone malformations, in particular of the femoral proximal portion, having such structural and functional features as to enable to regulate with precision and while operating, the angle of the cephalic screw that is fixed to the plate and the need to be able to perform an osteotomy in order to obtain a lateral translation of the femoral axis.

Another object of the invention is devising an inner femoral plate fixator device which enables the use of cephalic screws with a reduced diameter.

A further object of the invention is enabling to fix bone screws and the cephalic screw to the plate itself.

SUMMARY OF THE INVENTION

The idea of a solution underlying the present invention is providing a femoral plate divided in two components, proximal and distal, hinged to each other and locking means for locking the relative angular positioning of the two portions during the implanting of the plate thereof.

On the basis of such an idea of a solution, the technical problem is overcome by a device of the previously mentioned type and comprising:

a plate proximal portion, structurally independent from said elongated plate and hinged to the former at one of its shaped end;

at least a through hole to receive a cephalic screw in said plate proximal portion;

locking means located in proximity of the hinge point between the elongated plate and the proximal plate for locking the relative angular positioning of the two plates;

said locking means including at last a nut element abutting against a portion of the plate proximal portion thus removably linking the elongated plate and the proximal plate.

The shaped end is an end projection that is extended with a predetermined inclination angle α with respect to the plate longitudinal axis or otherwise to the plane where such axis lies.

Advantageously, said locking means comprise a pin or an eccentric nut active in a housing seat formed in a hinge element linking the elongated plate and the proximal plate.

The hinge element is a head at the end of said elongated plate.

The elongated plate has a proximal end shaped as an obelisk head and provided with a through hole transverse to its longitudinal axis and a lower part of the plate portion comprises a pair of stems respectively provided with transverse through holes which match with the through hole of said head when the plate proximal portion is pivotally mounted on the head.

It must be noted that the elongated plate has additional through holes located in the proximity of opposite longitudinal peripheral edges of the elongated plate; a hole located closer to the proximal hole for the bone screw and the other hole on the other side of the plate in the proximity of the opposite peripheral edge and in a location closer to the distal hole for the bone screw.

The eccentric nut is a hinge element between the elongated plate and the proximal plate portion and comprises stages, one of which is at least eccentric, that are inserted in a housing seat formed by adjacent holes having different diameters.

Each stage of said pin or nut is housed in a corresponding portion of the seat represented by a corresponding hole. The eccentricity of said eccentric stage is at least of 0.25 mm.

It must be noticed that cephalic screw is equipped with a head, a stem and an end distal portion with a thread with regular diameter and pitch; the stem having a diameter that is smaller than the diameters of the head and of the threaded distal portion. The cephalic screw stem has a diameter between 3 and 4 mm.

The features and the advantages of the fixator device according to the invention will be apparent by the hereinafter disclosure, of an exemplary non-limiting embodiment, referring to the enclosed drawings.

BRIEF DESCRIPTION OF THE DRAWINGS

FIG. 13 shows a side view of the inner fixator according to the variant of FIG. 12;

FIG. 14 shows a perspective view of a component of the inner fixator device according to the invention variant of FIG. 12;

FIG. 17 shows a perspective view of an additional detail of the inner fixator device according to the invention;

FIG. 21 shows a perspective view of an alternative embodiment of an inner fixator device according to the present invention;

FIGS. 27 and 28 are respective schematic cross-sectional views of the inner fixator of FIG. 21 in a regular and enlarged view respectively;

FIG. 30 shows another perspective view of the inner fixator of FIG. 29 taken from a different point of view;

FIG. 33 is a schematic cross-sectional view of the inner fixator of FIG. 29;

FIG. 34 is a schematic cross sectional enlarged view of a particular of the locking means incorporated into the inner fixator of FIG. 29.

Additional features and advantages of the inner fixator device of the invention will be apparent by the hereinafter disclosure, of a non-limiting exemplary embodiment, referring to the enclosed drawings.

DETAILED DESCRIPTION

Figure 1:
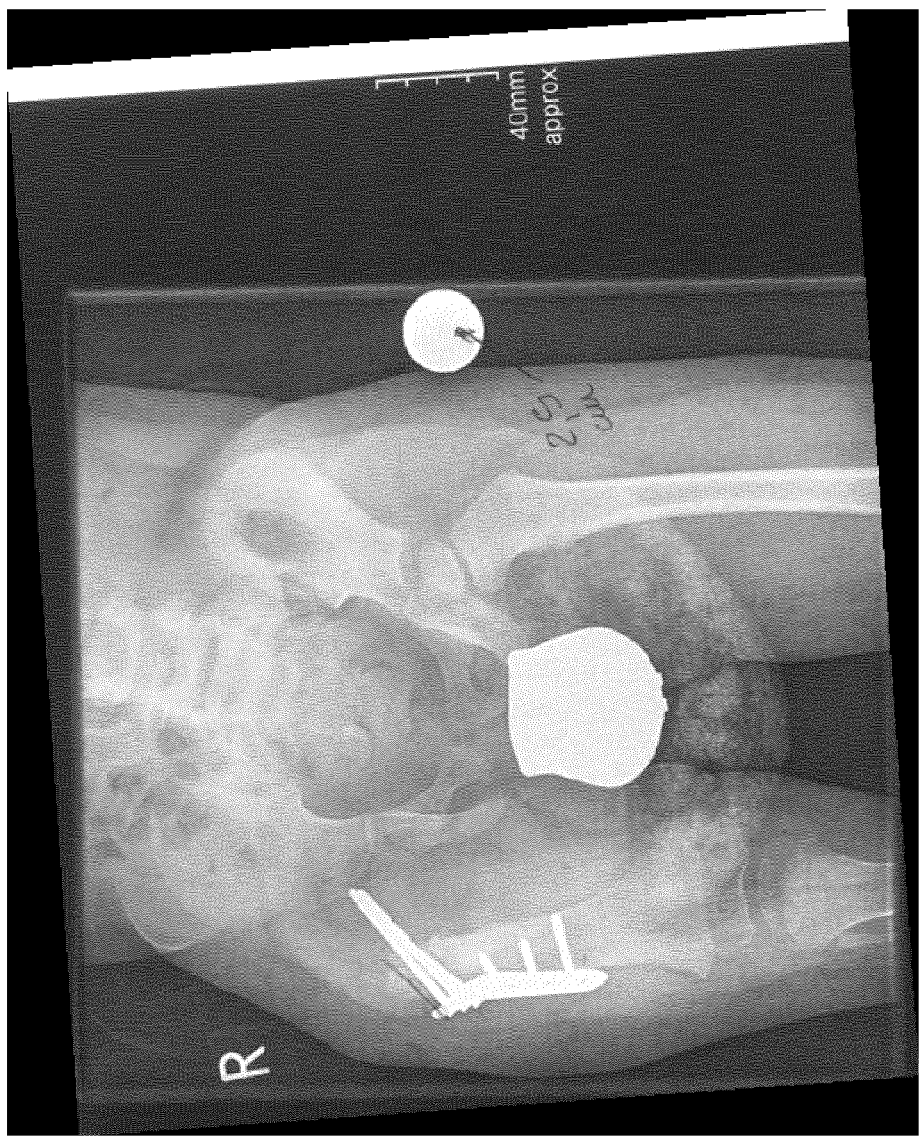
FIG. 1 shows an X-ray imaging of a pediatric patient who has been implanted an inner fixator device made according to the known art.
Figure 2:
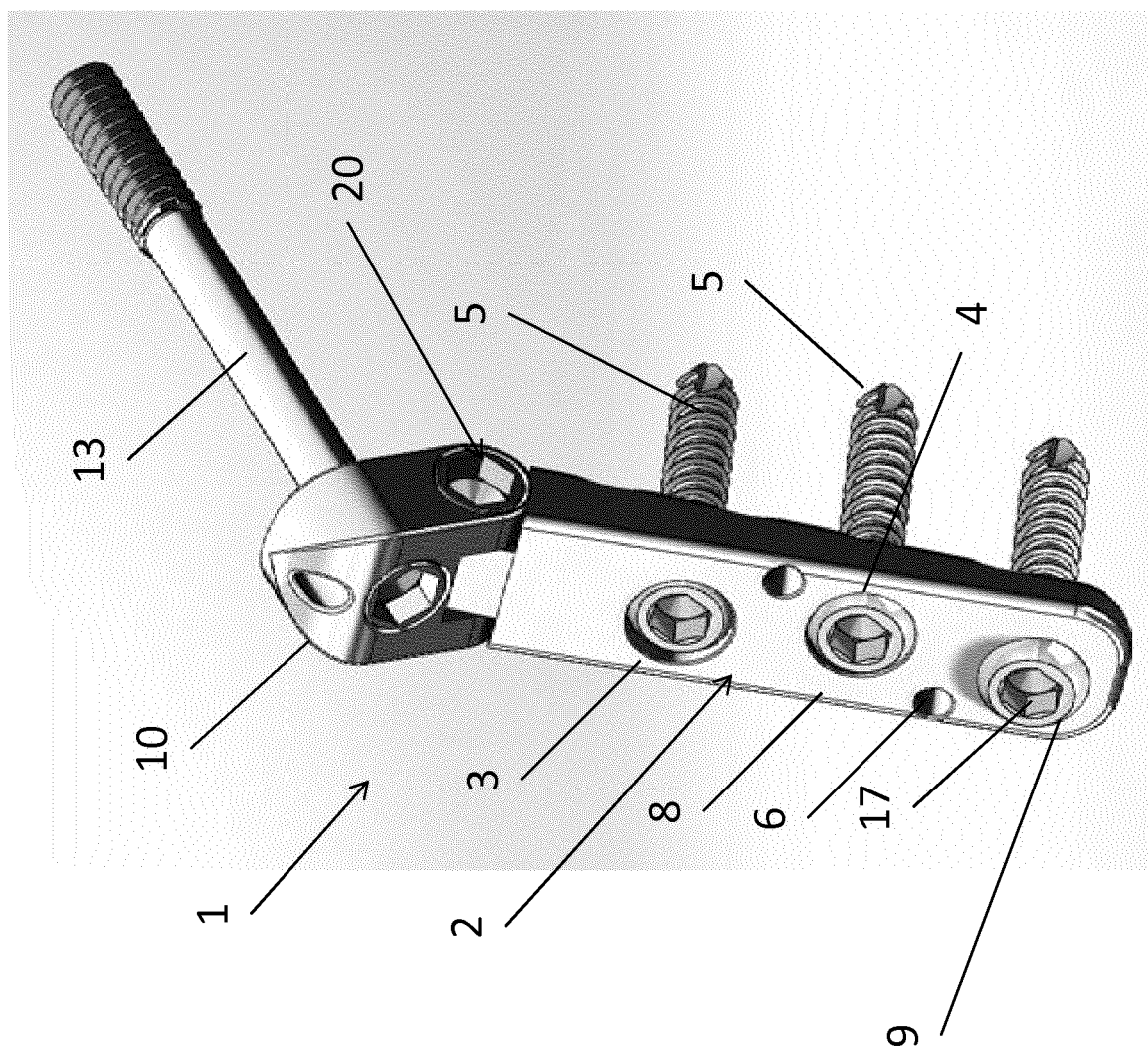
FIG. 2 shows a perspective view of an inner fixator device according to the present invention.
Figure 3:
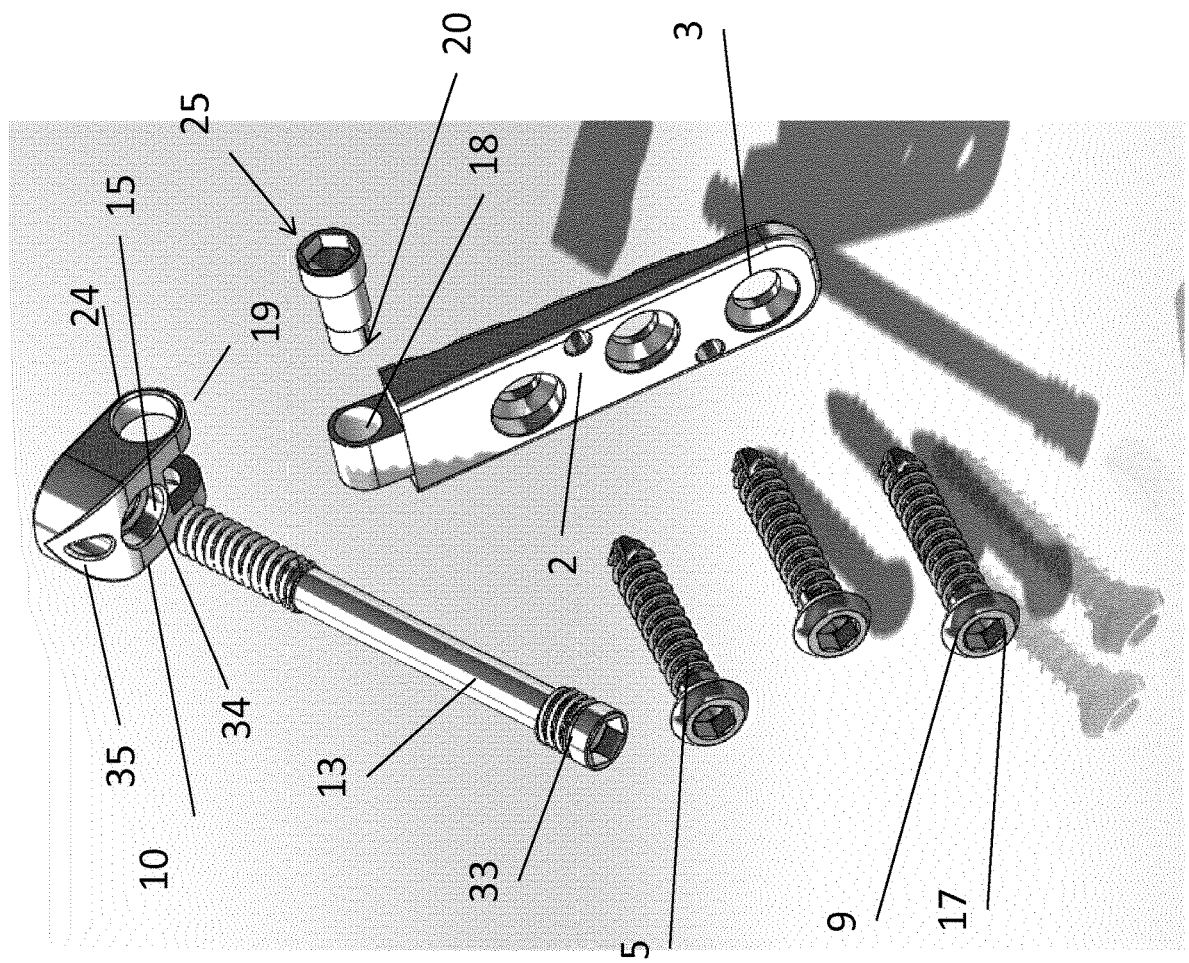
FIG. 3 shows a perspective view in separated parts of the device of FIG. 2.

Referring to such figures, and in particular to the embodiment of FIG. 2, an inner plate 2 fixator device for the correction of severe bone malformations is globally and schematically indicated by 1.

The fixator device 1 of the present invention is particularly suitable, though not exclusively, for the pediatric reconstruction of severe malformations of the femoral proximal portion, such as for example the missing or wrong positioning of the femoral head or of the femoral neck.

Device 1 comprises a first elongated and flattened plate component 2 in which through holes 3, 4 are provided for receiving bone screws 5. The plate 2 has an elongated trapezoidal shape with a wedge-shaped profile to reduce its volume, however such shape shall be without limitation for the Applicant's rights.

In the herein described non-limiting exemplary embodiment, there are totally 3 holes 3, 4 for the bone screws, though there is nothing to prevent them from being a higher or lower number.

Referring to the femoral head position, we shall define the hole 3, which is more proximal to the head, as the proximal hole of the plate 2 and the other hole 3 as the distal hole of plate 2.

Holes 3 are aligned one another and parallel to or crossed by a longitudinal axis x-x of plate 2. In one alternative embodiment the holes 3 are always aligned one another, though slightly off-axis with respect to the longitudinal X-X axis of plate 2.

The hole 4 is intermediate with respect to holes 3 and is eccentric with respect to the longitudinal axis X-X of plate 2.

All the holes 3 or 4 may be provided with an inner thread for receiving bone screws 5 having a head 9 peripherically threaded and provided with an hex key seat 17.

Figure 4:
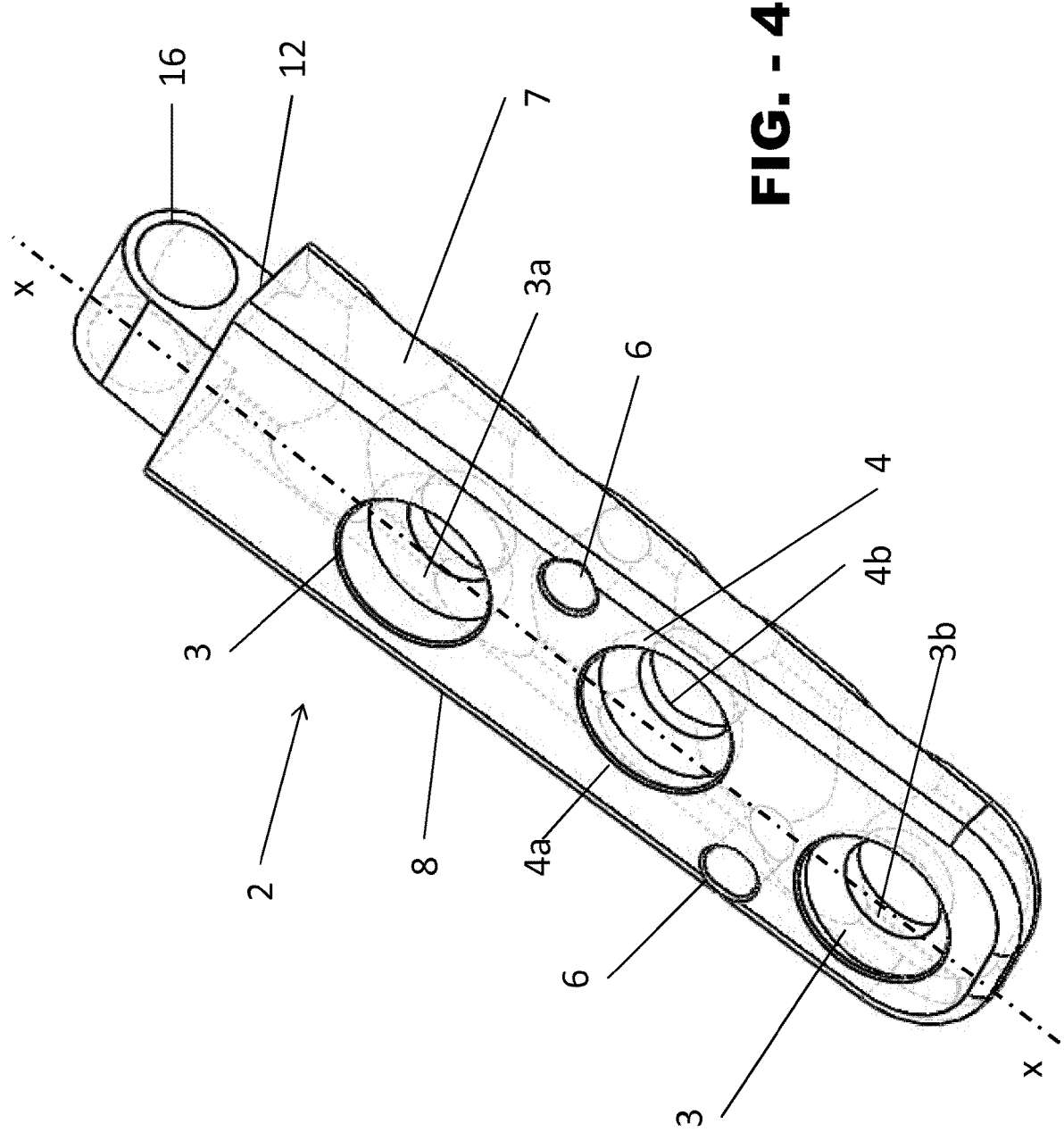
FIG. 4 shows a perspective view of a component of the inner fixator device according to the present invention.
Figure 5:
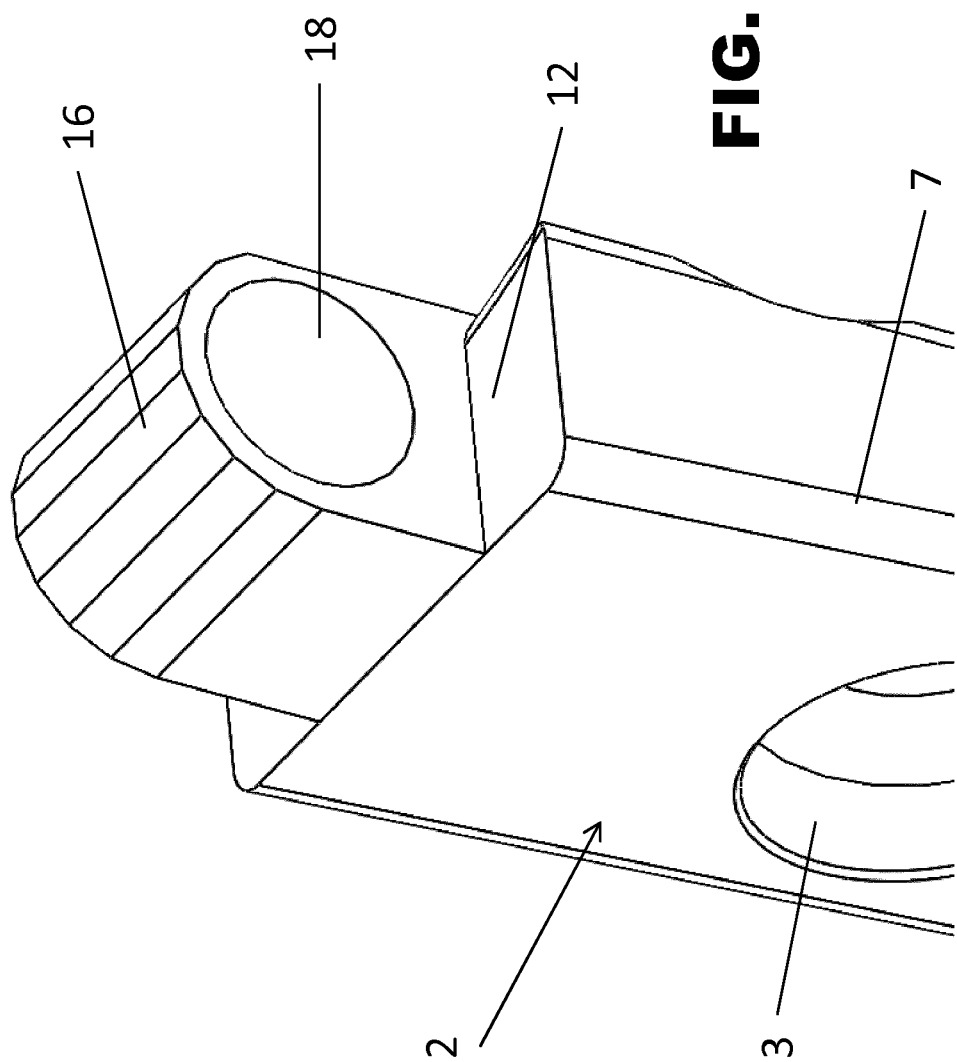
FIG. 5 shows an enlarged scale perspective view of a detail of proximal end of the component of FIG. 4.
Figure 6:
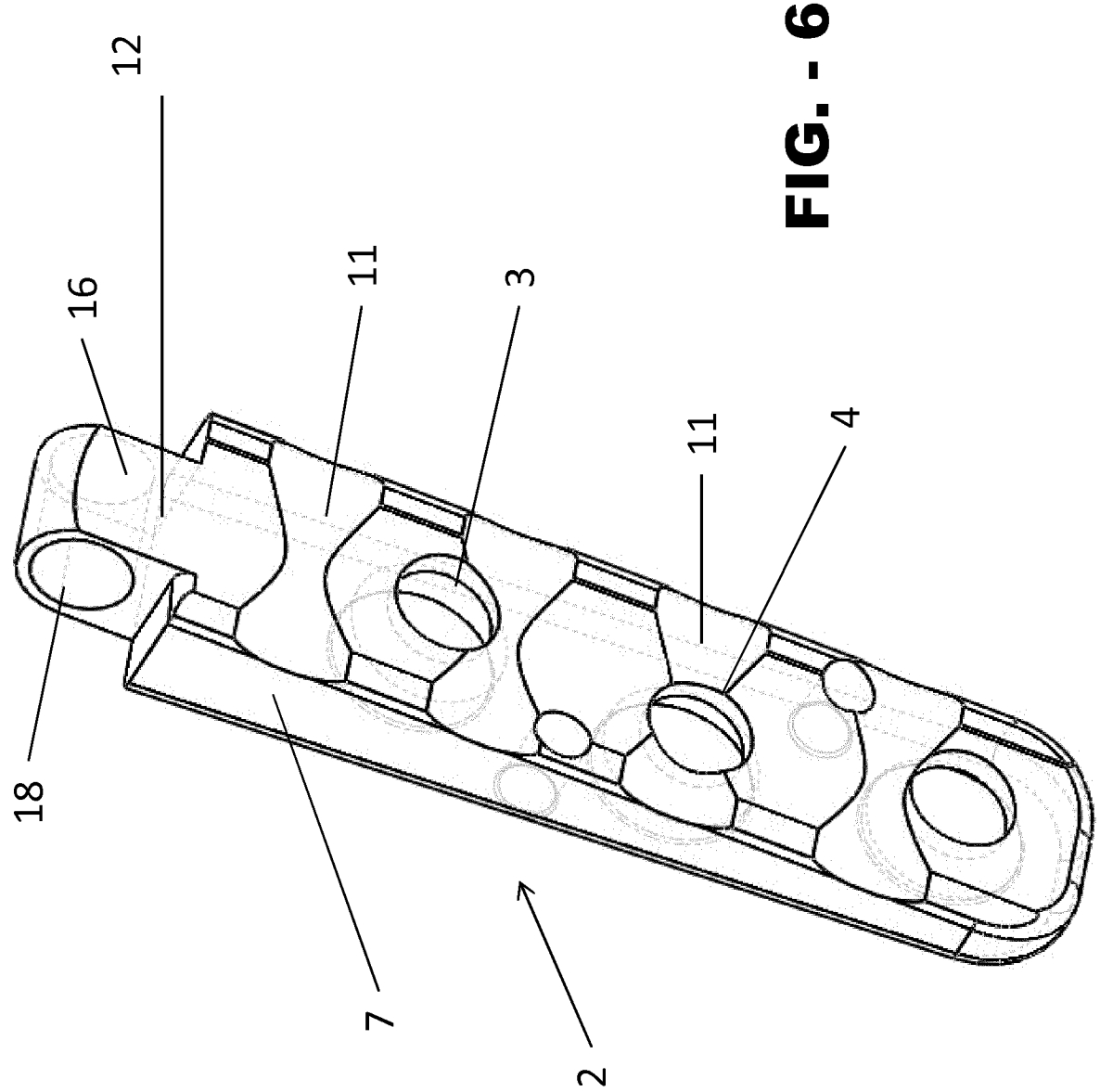
FIG. 6 shows a perspective view of the component of FIG. 4 according to an opposite observation point.
Figure 7:
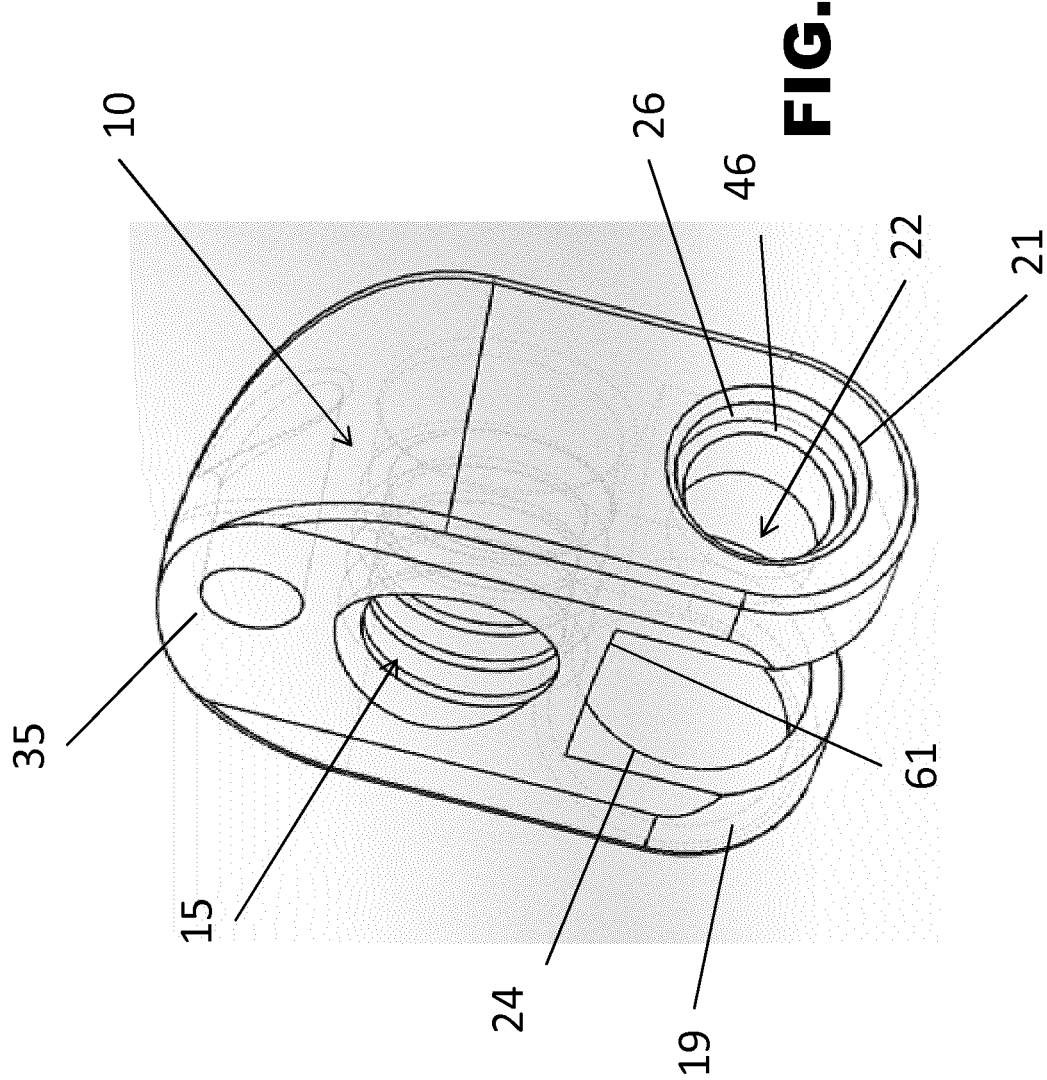
FIG. 7 shows a perspective view of a component of the inner fixator of the present invention.

In a preferred embodiment, holes 3 and 4 have a counterbore which differentiates the diameter into two coaxial portions 3a and 3b or 4a and 4b, as clearly shown in FIG. 4. This allows to thread only the hole with the smallest diameter, for example 3b or 4b, to insert angular stability screws 5.

There are also other through holes 6, with smaller diameter with respect to holes 3, 4 for bone screws. Such additional through holes 6 are intended to house wires K for fixing or temporarily stabilizing the bone to the plate 2. These wires usually have a diameter smaller than 1.6 mm.

More particularly, these through holes 6 are located in the proximity of opposite longitudinal peripheral edges 7, 8 of the plate 2, a hole 2 located closer to the proximal hole 3 and the other hole 6 on the other side of the plate 2 in the proximity of the opposite peripheral edge 8 and in a location closer to the distal hole 3.

It must be noted that the lower surface of the elongated plate 2 is for example shaped with some hourglass-shaped recesses 11 to promote the vascularization of the tissues adhering to the bone subjected to the surgery.

The elongated plate 2 has a proximal end 12 shaped and formed as an obelisk head 16 as well as provided with a through hole 18 transversal to the longitudinal axis x-x of the elongated plate 2.

On this proximal shaped end 12 a second component of the inner fixator 1 is pivotally mounted, that is, a plate proximal portion 10, structurally independent from the elongated plate 2 and hinged to the latter at the head 16.

The overall longitudinal extension of device 1 such as it is structured is of about just 40 mm.

More particularly, the plate 10 proximal portion has a lower part intended to be arranged on the head 16 of the proximal end of the elongated plate 2.

This lower part of the plate portion 10 comprises a pair of parallel stems 19, 21 respectively provided with transverse through holes 24, 26 which match with the hole 18 of the head 16 when the plate proximal portion 10 is pivotally mounted on the head 16.

At least one 24 of the holes has a higher diameter with respect to the other hole 26.

The triad of through holes 24, 18 and 26, aligned one another when the plate portion 10 is mounted on the head 16, defines a housing seat 22 of a hinge element 25 linking the elongated plate 2 and the plate portion 10. The seat 22 is substantially formed of adjacent holes but having different diameters.

The hinge element 25 is a pin or a nut with several stages 28, 29, 30, the intermediate stage 29 of which is eccentric with respect to the other two and is inserted and active in said housing seat 22 to block the relative angular positioning of the two plates 2 and 10.

Each stage 28, 29 and 30 of said pin or nut 25 is housed in a corresponding portion of the seat 22 represented and defined by the union of a corresponding hole 26, 18 and 24.

Stages 28, 29 and 30 of the pin or nut 25 have the intermediate stage 29 that is eccentric with respect to the other two and, preferably, with an eccentricity of at least 0.25 mm.

Thanks to this slight eccentricity, a little angular rotation of the nut 25 in the seat 22 is sufficient to block in situ by interference the relative angle position between the elongated plate 2 and the plate proximal portion 10 according to the needs established by the orthopedic surgeon.

Substantially, the seat 22 and the pin or nut 25 form locking means 20 which cooperate to fasten the relative angular positioning between the elongated plate 2 and the plate proximal portion 10. Therefore, said locking means 20 includes at last a nut element 25 abutting against a portion 22 of the plate proximal portion 10 thus removably linking the elongated plate 2 and the proximal plate 10.

The first stage 28 of the nut 25 has a hexagonal recess seat 32 for inserting an operating tool, for example an hex wrench.

The last stage 30 of the nut 25 has a free end which has a conic recess 31 to plastically rebut the eccentric. The hole 24 has a higher diameter with respect to the hole 26 provided in the stem 21 of the plate proximal portion 10. The hole 26 of the stem 21 internally provides a further reduction of diameter 46 which is used to prevent the last stage 30 of the stage nut 25 from exiting.

Figure 15:
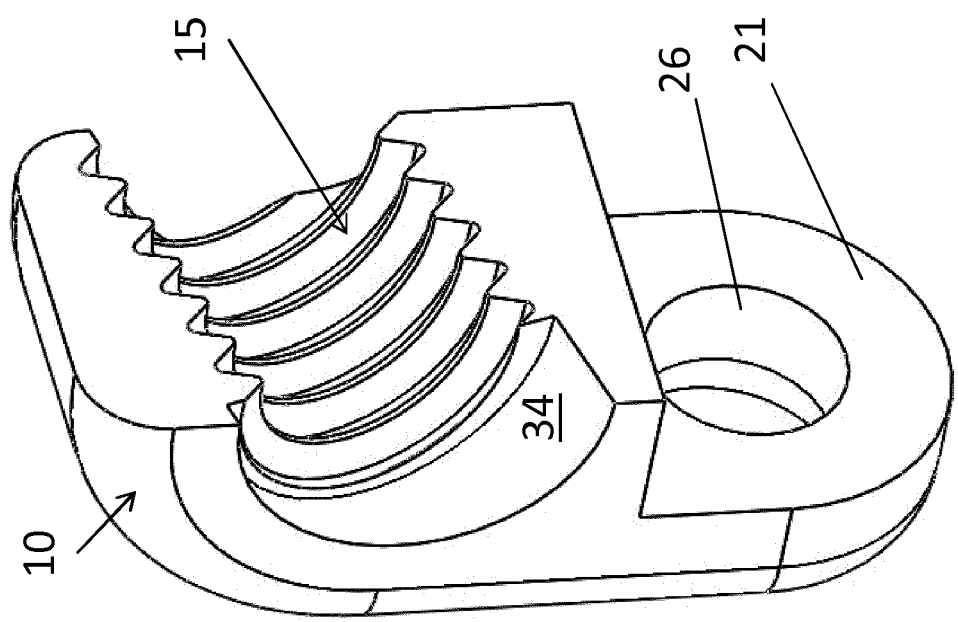
Figure 18:
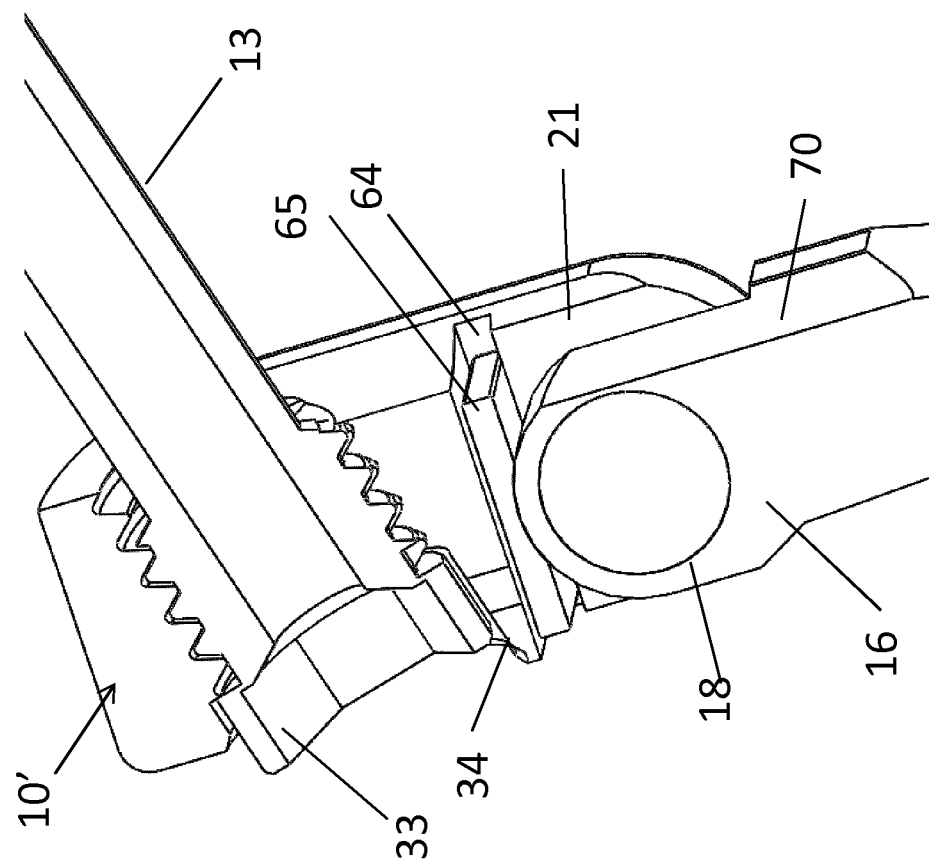
FIG. 18 shows a sectional side view on a vertical plane of the detail of FIG. 17 of the inner fixator device according to the invention.

Advantageously, according to the invention, a through hole 15 is obtained in the plate proximal portion 10 in an almost central position to receive a cephalic screw 13. More particularly, such hole is illustrated in detail in the FIGS. 15 and 16 which show that the hole 15 is obtained through a preferred inclination angle β with respect to a transverse axis y-y of the plate proximal portion 10. Such inclination is of about 35° and further eases the correct positioning of the cephalic screw in cooperation with the angulation obtained from the hinge link of the two plate-shaped components 2, 10 of the fixator 1.

The hole 15 is internally threaded to engage the screwing of a threaded head 33 of the cephalic screw 13. However, an inner counterbore is also provided which represents an end stop 34 for the head 33 of the cephalic screw.

Such counterbore is arranged at the same inclination of the threaded hole 15 so as to receive the greater part of the head 33 of the cephalic screw.

The cephalic screw 13 is preferably cannulated; but it can also be full. The screw 13 of the present invention has some unconventional hereinafter described peculiarities.

It is provided with a head 33, a stem 36 and an end distal portion with a regular diameter and pitch thread.

A thread 38 is provided at the head 33 for the proximal engagement of the plate proximal portion 10 into the hole 15.

The head 33 has a hexagonal recess seat 39 for inserting an operating tool, for example an hex wrench. The seat 39 also allows access to the cannulated portion of the cephalic screw 13.

The stem 36 has a smaller diameter than the diameter of the head 33 and than diameter of the threaded end 37. Such a peculiarity enables to insert the screw also into small diameter femoral necks and allows the bone growth on the diameter thereof, considering the patients' pediatric age. The stem diameter may also be of just 3 or 4 mm.

A stop end abutting edge 40 is provided between the head 33 and the threaded proximal portion 38 intended to impact against the inner counterbore 34 of the hole 15 of the plate proximal portion 10.

The cephalic screw 13 structure is completed by some flat portions 41 formed in the first threads close to the stem 36 of the threaded distal portion 37, in order to provide the femoral head with greater rotational stability when the screw 13 is installed.

In order to reduce the cut-out effect while being inserted, the tip 42 of the screw 13 has been rounded.

It must be underlined that an additional through hole 35 is provided in the upper portion of the plate proximal portion 10 intended to receive a first stabilization wire, not shown in the drawings since it is conventional. Such a wire may for example have a maximum diameter of 1.6 mm.

Figure 10:
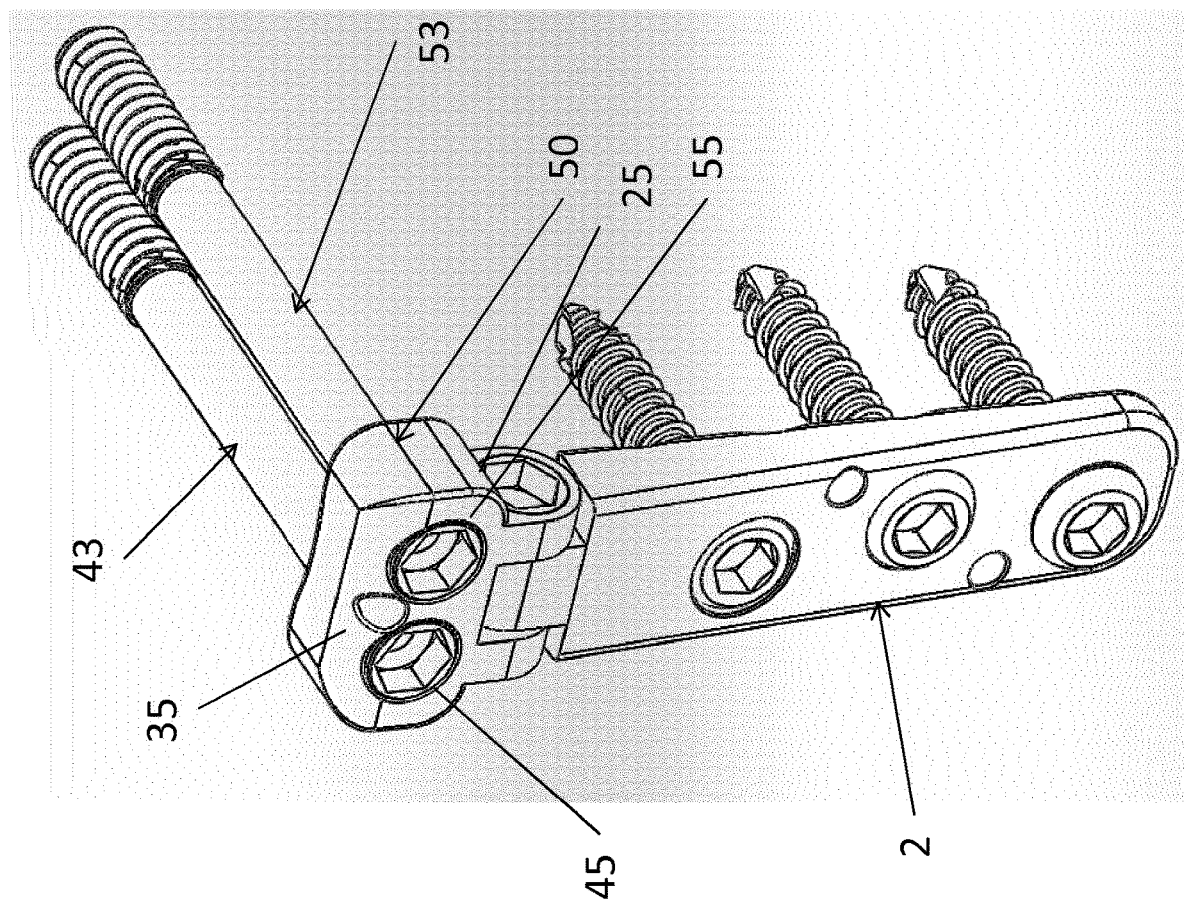
FIG. 10 shows a perspective view of a second embodiment of the inner fixator device according to the invention.
Figure 11:
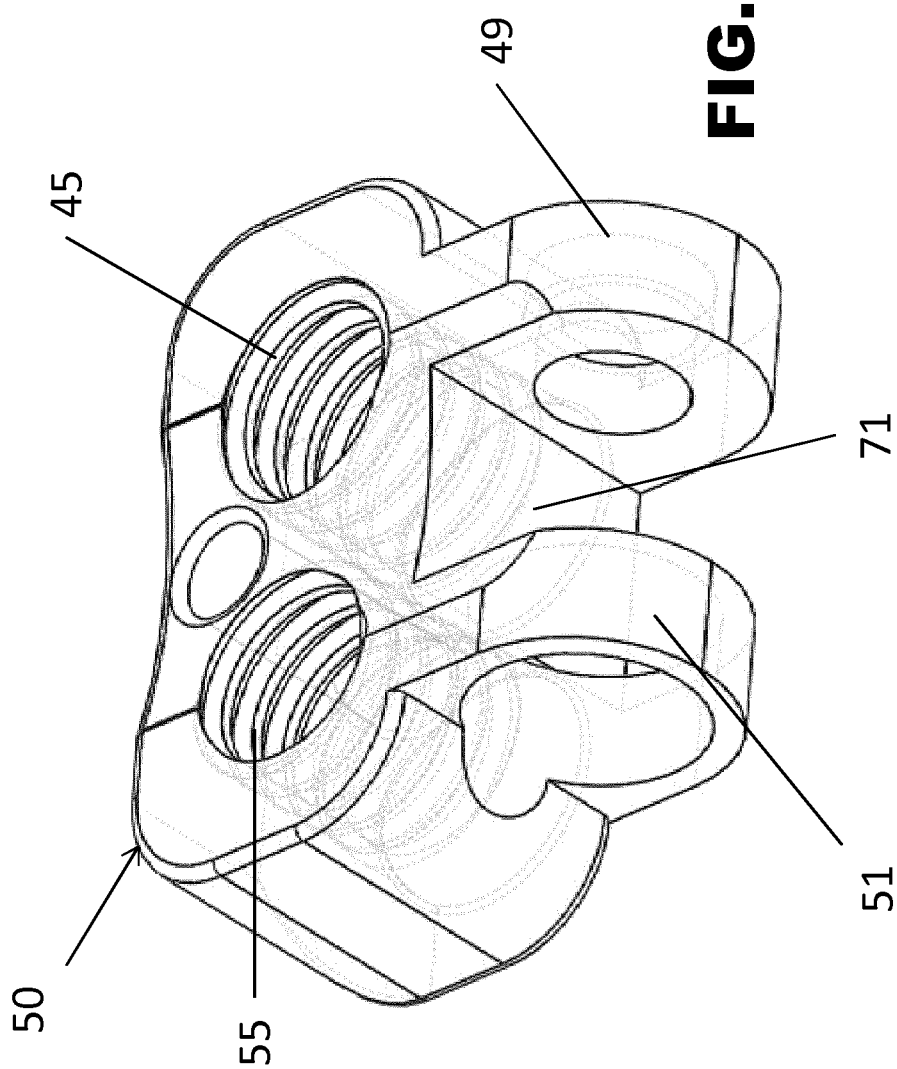
FIG. 11 shows a perspective view of an inner fixator device according to the present invention.
Figure 12:
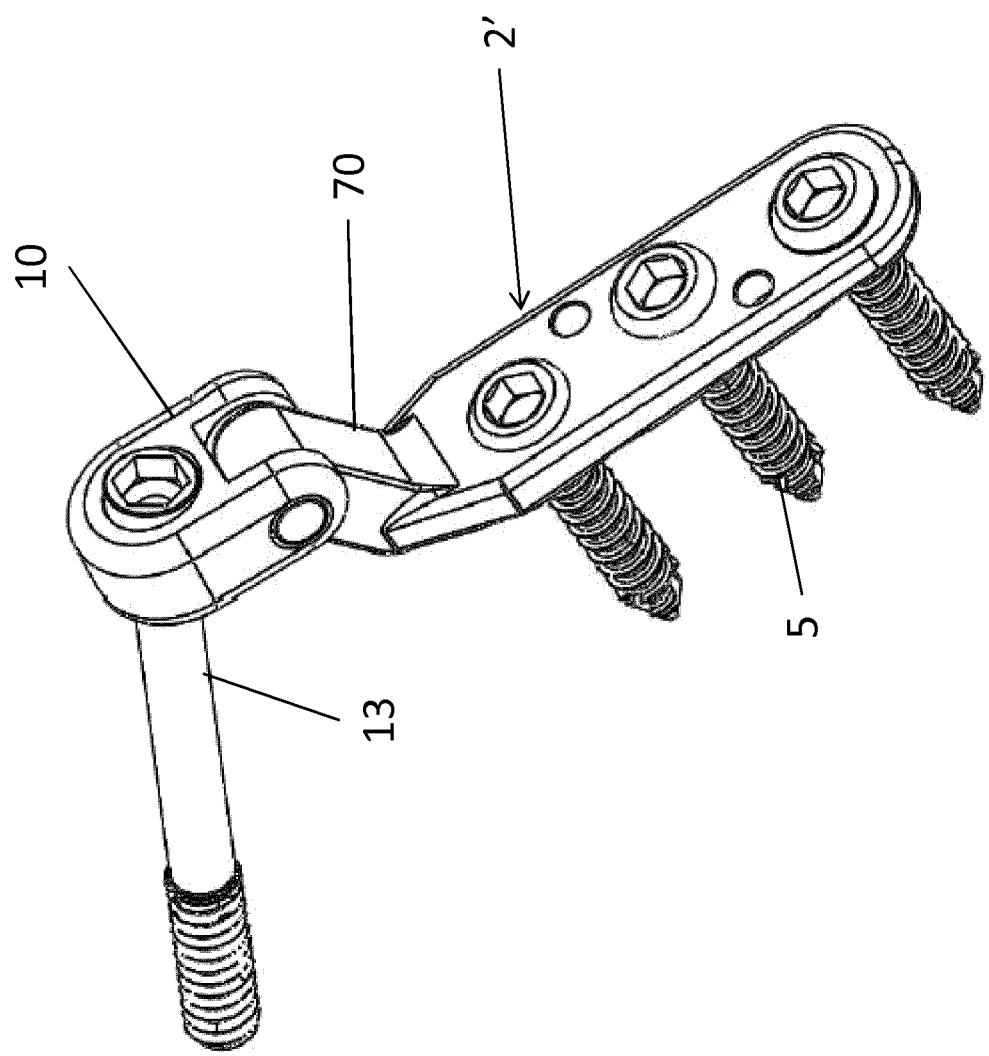
FIG. 12 shows a perspective view of a variant embodiment of the inner fixator device according to the present invention.

In a variant embodiment, illustrated for example in FIGS. 10 and 11, a plate proximal portion 50 is provided with a pair of parallel, internally threaded, holes 45, 55 to receive a pair of cephalic screws 43, 53.

Holes 45, 55 may also have a smaller diameter than the one of the hole 15 described in the previous embodiment.

Cephalic screws 43, 53 are structurally identical to the cephalic screw 13 of the previous embodiment, but they may have smaller dimensions and diameter, though maintaining the same proportions.

Locking means 20 for fastening the relative angular positioning between the elongated plate 2 and the plate proximal portion 50 of this second embodiment are at all identical to the previously described ones.

The plate proximal portion 50 too has a pair of stems 49, 51 which wrap the head 16 of the elongated plate 2 when the plate proximal portion 50 is pivotally mounted on the elongated plate 2 end 12 of the fixator device 1.

It is rather clear from the previous description how the inner fixator device according to the invention may be used.

The decision on the positioning angle between the two plates 2 and 10 or 2 and 50 is taken by the orthopedic surgeon in the operating room so as to adapt to the situation thereof.

The plate proximal portion 10 or 50 is linked to the femoral neck or on the femoral head; then, the elongated plate 2 is adhered to the femoral part and the two hinged plates are fastened in the relative angular position by simply locking them through a relatively slight rotation of the eccentric nut 25.

The action on the pin or nut 25 allows to quickly stabilize the proximal part of device 1 with the distal part, that is the elongated plate 2, into any one relative position.

Locking occurs as follows: the rotation of pin 25 also leads the intermediate stage 29 to rotate so that the eccentric portion interferes with a receiving portion, e.g. the lower surface 61 of the plate proximal portion 10 or the lower surface 71 of the other plate proximal portion 50.

The eccentric stage 29 of the nut 25 remains locked with interference inside seat 22 which is in turn composed of through holes with different diameters. The friction force resulting from the simple rotation of nut 25 opposes the outer rotation forces which would tend to open the two composing parts 2 and 10 of device 1.

The materials used to implement the inner fixator device 1 are materials conventionally suitable for surgical implantation, that is to say titanium and its alloys.

In a variant embodiment illustrated for example in the Figures from 12 on, a fixator 1 plate 2' has its end 12 shaped into an end projection 70 that is extended with a predetermined inclination angle α with respect to the plate 2' longitudinal axis X-X, or otherwise to the plane where such axis X-X lies.

Such end projection 70 has the function to stretch out and translate the head of the shaped proximal end 12 of plate 2' to form a protruding head 16' wherein the through hole 18 is obtained to link the other component of the inner fixator 1, that is the plate proximal portion 10, hinged at the head 16'.

Other features of plate 2' structurally and functionally identical to plate 2 of the first embodiment will be indicated in the figures by the same reference numbers. The same can be said for the plate proximal portion 10.

The projection 70 inclination angle α may be comprised between 30° and 45°; however, it will preferably be chosen in order to determine a substantially parallel translation of the hinge point of the plate proximal portion 10 with respect to the plane of the plate 2' provided with through holes 3, 4 or with holes 6 for stabilization wires.

Depending on the needs, such translation may be of different magnitude, e.g.: 6 mm, 8 mm, 10 mm according to the translation magnitude required to place the femoral axis into a correct position.

All the structural features disclosed referring to the previous embodiments are intended to be combinable to and with this variant embodiment unless not expressly and admittedly provided.

Finally, referring in particular to Figures from 17 to 20, an additional embodiment is shown wherein locking means 20 have been refined to fasten the relative angular positioning of the two plates 2, 2' and 10 or 2, 2' and 50.

In particular, a slot 64 has been obtained at the lower surface 61 of the plate proximal portion which will be indicated by the numeral 10' for this structural modification.

Slot 64 is arranged between the lower arms 19 and 21 junction of the plate proximal portion 10'.

Figure 20:
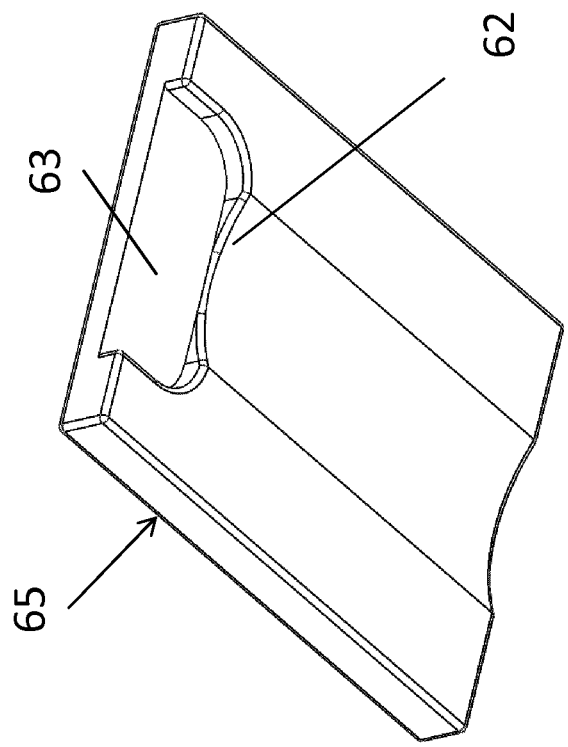
FIGS. 19 and 20 respectively show detail perspective views of the detail of the inner fixator device according to the invention.
Figure 19:
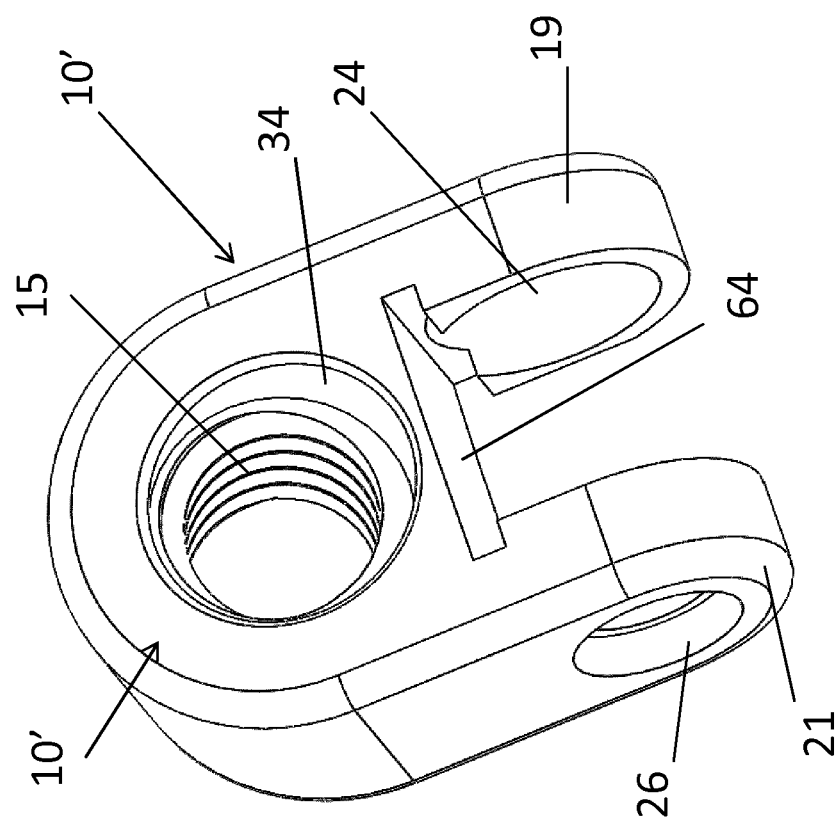
Figure 23:
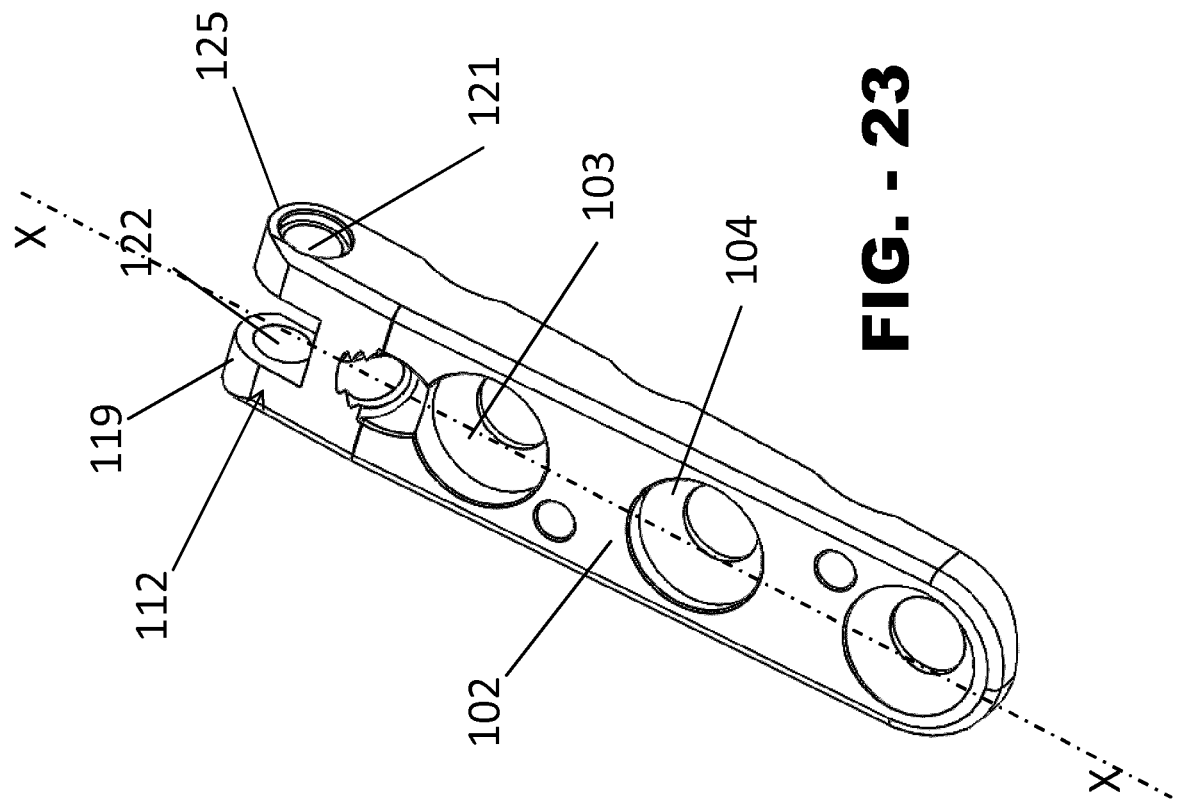
FIGS. 22 and 23 shows another perspective view of the inner fixator of FIG. 21 taken from a different point of view.
Figure 22:
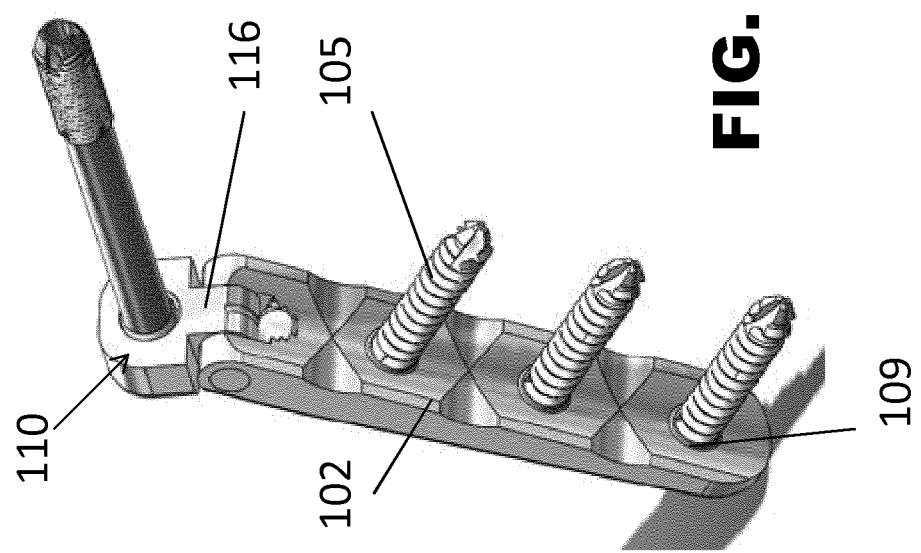
Figure 24:
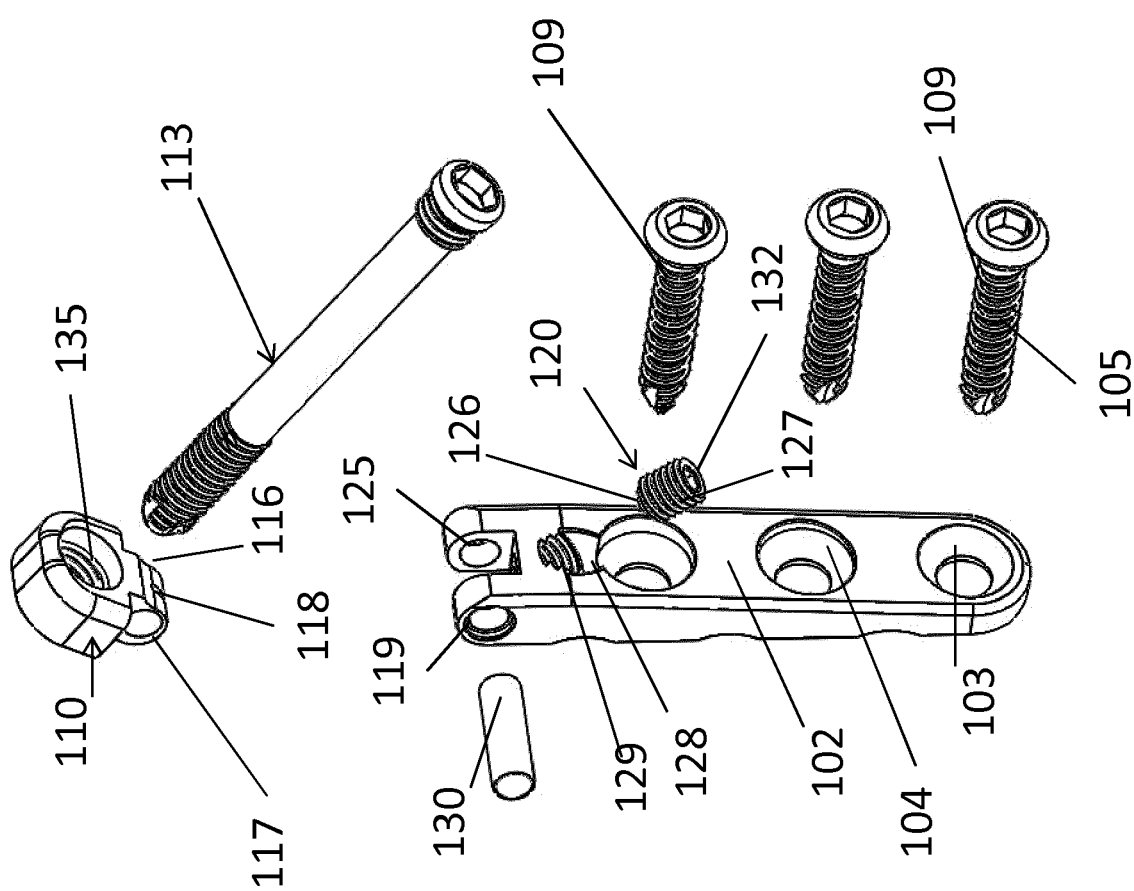
FIG. 24 shows a schematic perspective view of the inner fixator of FIG. 21 in all its components parts.

In such slot 64 a platelet 65 is inserted as shown in FIG. 20 in its structural conformation which also provides a lower shaping with a concave profile 62 and an end slot 63.

Platelet 65 is substantially plane except for shaping 62 and it is intended to increase the hold between the end of head 16 or 16' and the plate proximal portion 10 or 10'.

The rotation of the pin or nut 25 makes rotate the eccentric intermediate stage 29 which pushes the platelet 65 and moves it slightly making it abut against the lower surface of the plate proximal portion 10, 10'.

Thereby, the closing pair does not lose friction and the contacting surface between the head 16, 16' of the plate 2, 2' and the other plate portion 10, 10' increases. Substantially, the eccentric push is amplified by a greater contacting surface between locking means components.

Now, with more specific reference to the embodiment of the figures from 21 to 28, it will be disclosed an alternative embodiment of the inner fixator device according to the present invention. We will refer to this embodiment with the numeral 101 and following.

Other components of the fixator 101 corresponding to the components disclosed for the first embodiment of the fixator 1 will be identified with the same reference numbers of the first embodiment increased by a factor of 100.

The overall longitudinal extension of device 100 such as it is structured is of about just 50 mm.

As in the previous embodiments, the fixator 100 includes a first elongated and flattened plate component 102 in which through holes 103, 104 are provided for receiving bone screws 105. These holes have an opening recessed portion having a diameter slightly larger than the head of the screws 105 and a narrower bottom portion slightly larger than the screws stem.

All the holes 103 or 104 may be provided with an inner thread in the opening portion for receiving the peripherically threaded head 109 of the screws. In alternative, it is possible to thread only the hole with the smallest diameter, for example the bottom hole, to insert angular stability screws 105 as in the first embodiment previously disclosed.

The holes may be aligned along the plate longitudinal axis X-X or misaligned as in the previous embodiments with the intermediate hole 104 slightly eccentric with respect to the longitudinal axis X-X of plate 2.

Differently from the previous embodiments, the elongated plate 102 has a proximal end 112 shaped and formed as a fork element with a couple of short stalks or embanks 119, 120 each having a respective through hole 121, 122 transversal to the longitudinal axis X-X of the elongated plate 102.

On this proximal shaped end 112 a second component 110 of the inner fixator 101 is pivotally mounted.

A plate proximal portion 110, structurally independent from the elongated plate 102 and hinged to the latter between the couple of stalks 119, 125.

This plate proximal portion 110 has a through hole 135 for hosting a cephalic screw 113 structure similar to the one disclosed in the previous examples.

The upper portions of these stalks 119, 125 are rounded to allow a smoother movement of the plate proximal portion 110.

More particularly, the plate 110 proximal portion has a lower projecting part 116 intended to be arranged between the stalks 119, 125 of the proximal end of the elongated plate 102.

This projecting part 116 has a passing hole 117 that may be aligned with the holes 121, 122 when the projecting part 116 is hinged between the stalks 119, 125.

Figure 26:
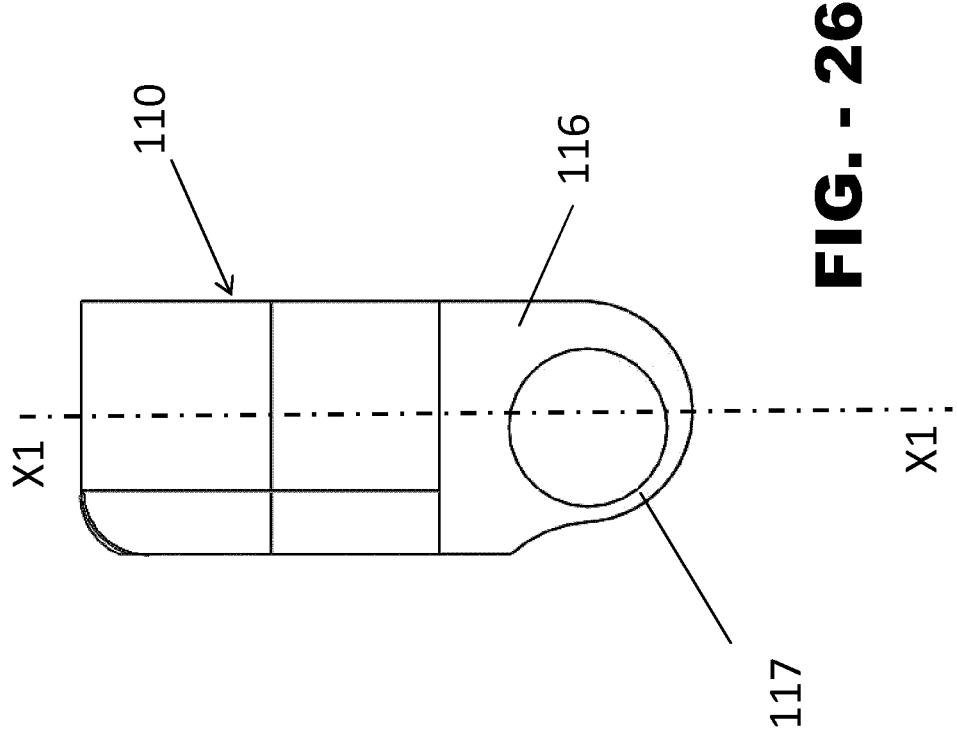
FIG. 26 is a schematic lateral view of the portion of FIG. 25.
Figure 25:
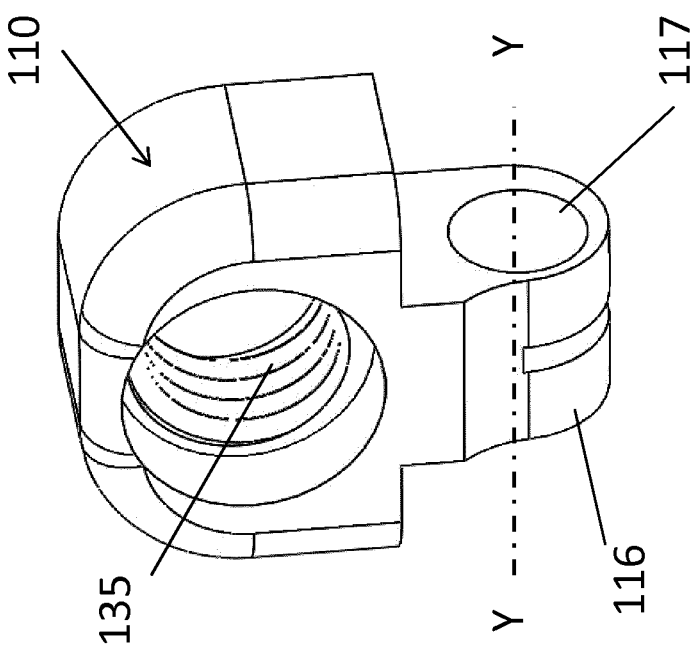
FIG. 25 is a perspective view of a portion of the inner fixator of FIG. 21.

As shown in FIG. 26, the hole 117 is slightly eccentric with respect to the middle axis X1-X1 of the plate proximal portion 110 and with respect to the other holes 121, 122 that are centrally realized in their respective stalks portions 119, 125. This eccentric portion impedes the movement of the proximal portion 110 after it has been locked by the desired angular position as will appear from the following description.

A pin 130 is transversally inserted through the three aligned holes 121, 117 and 122 to hinge the two plate portions 102 and 110, distal and proximal, of the inner fixator 100.

Advantageously, locking means 120 are located in proximity of the hinge point between the elongated plate 102 and the proximal plate 110 for locking the relative angular positioning of the two plates.

Said locking means 120 includes at last a nut element 127 abutting against a portion 116 of the plate proximal portion.

More specifically, the nut element 127 is hosted inside a hole 128 that presents an internally threaded portion 129.

This hole 128 is realized close to the upper proximal hole 103 of the elongated distal plate 102. However, the axis of the hole 128 is inclined with respect to the axis of the proximal hole 103 so that the hole 128 opens in the interspace between the stalks 119 and 125.

The nut element 127 has a sharp and conical end 126 that projects toward the interspace between the stalks 119 and 125 when the nut element 127 is screwed inside the threaded portion 129.

The nut element 25 has an hexagonal recess seat 132 for inserting an operating tool, for example an hex wrench.

In this manner the sharp end 126 gets in touch with the projecting portion 116 of the proximal plate 110 thus locking the relative angular positioning of the two plates 102 and 110.

This link is removable in the sense that a release action on the nut element 127 allows changing the relative angular positioning of the two plates 102 and 110.

To allow a better holding force, a slot 118 is provided at one end of the projecting portion 116 of the proximal plate 110 facing the interspace between the stalks 119, 125 to allow an insertion of the sharp end 126 of the nut element 127 inside such a slot 118.

Advantageously, the nut element 127 is initially inserted through the back of the plate 102 where the hole 128 opens in the interspace between the stalks 119, 125 since the open entrance of the hole 118 has a reduced diameter 131 to impede the exit from the front side of the nut element 127.

With more specific reference to the embodiment of the figures from 29 to 34, it will be disclosed a third alternative embodiment of the inner fixator device according to the present invention.

In this second embodiment the fixator device of the present invention is illustrated with the numbers 201 and following and comprises a first elongated and flattened plate component 202 in which through holes 203, 204 are provided for receiving bone screws 205.

The shape of the plate 202 is similar to the first embodiment previously disclosed. The scope and presence of the holes 203 and 204 is equivalent to the holes 3 and 4 disclosed with reference to the first embodiment and we will avoid a further description to reduce the length of the present specification.

This is also true for the other through holes 206 that are provided with a smaller diameter with respect to holes 203, 204 for bone screws. Such additional through holes 206 are intended to house wires K for fixing or temporarily stabilizing the bone to the plate 202.

Other components of the fixator 201 corresponding to the components disclosed for the first embodiment of the fixator 1 will be identified with the same reference numbers of the first embodiment increased by a factor of 200.

Even in this case the lower surface of the elongated plate 202 is shaped with some hourglass-shaped recesses 211 to promote the vascularisation of the tissues adhering to the bone subjected to the surgery.

The elongated plate 202 has a proximal end 212 shaped and formed as an obelisk head 216 as well as provided with a through hole 218 transversal to the longitudinal axis X-X of the elongated plate 202.

On this proximal shaped end 212 a second component of the inner fixator 200 is pivotally mounted as in the first embodiment. A plate proximal portion 210, structurally independent from the first elongated plate 202 is hinged to head 216 of the first plate 202.

The overall longitudinal extension of device 201 such as it is structured is of about just 50 mm.

The plate proximal portion 210 has a lower part 214 intended to be arranged on the head 216 of the proximal end of the elongated plate 202.

This lower part 214 of the plate portion 210 comprises a pair of parallel stems 219, 221 respectively provided with transverse through holes 224, 226 which match with the hole 218 of the head 216 when the plate proximal portion 210 is pivotally mounted on the head 216.

At least one 224 of the holes has a higher diameter with respect to the other hole 226.

The triad of through holes 224, 218 and 226, aligned one another when the plate portion 210 is mounted on the head 216, defines a housing seat 222 of a hinge element 225 linking the elongated plate 202 and the plate portion 210. The seat 222 is substantially formed of adjacent holes but having different diameters.

Figure 8:
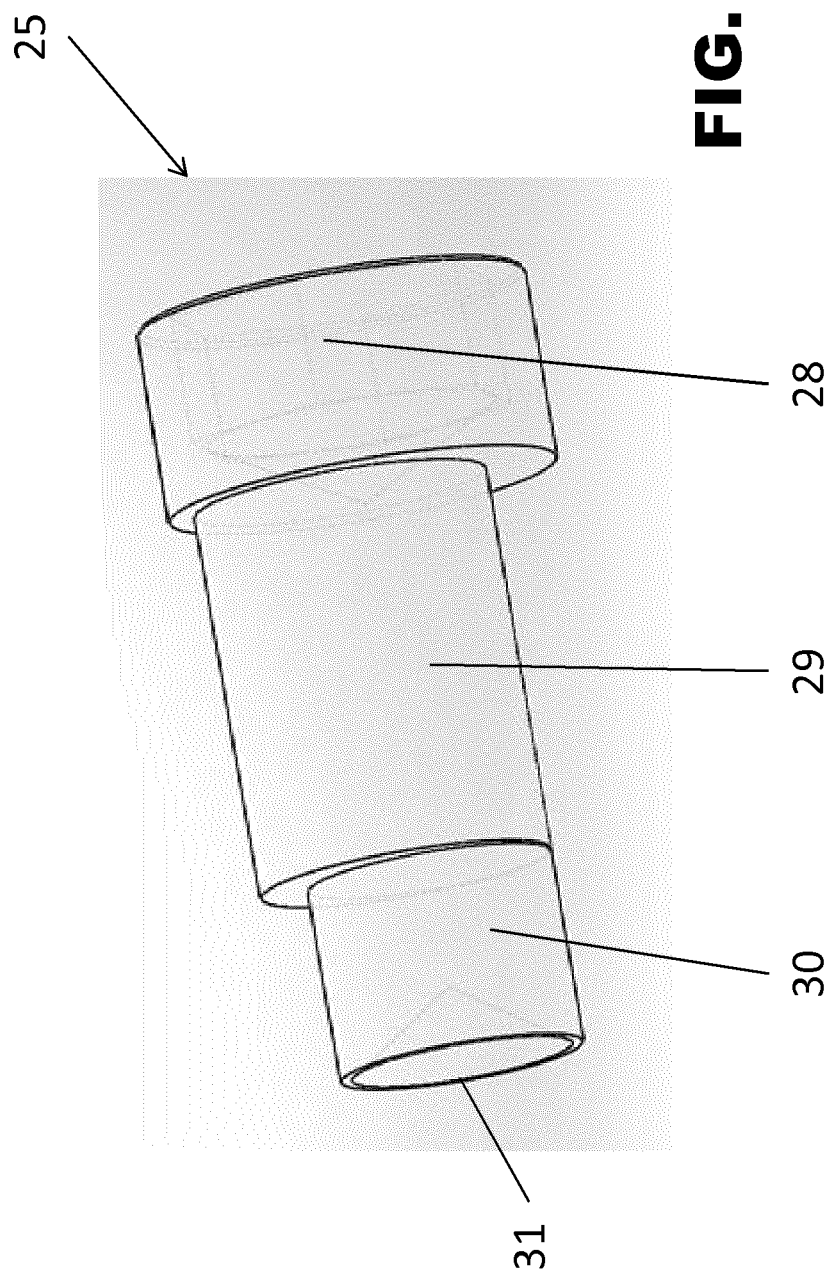
FIG. 8 shows a perspective view of an additional component of the inner fixator of the present invention.
Figure 9:
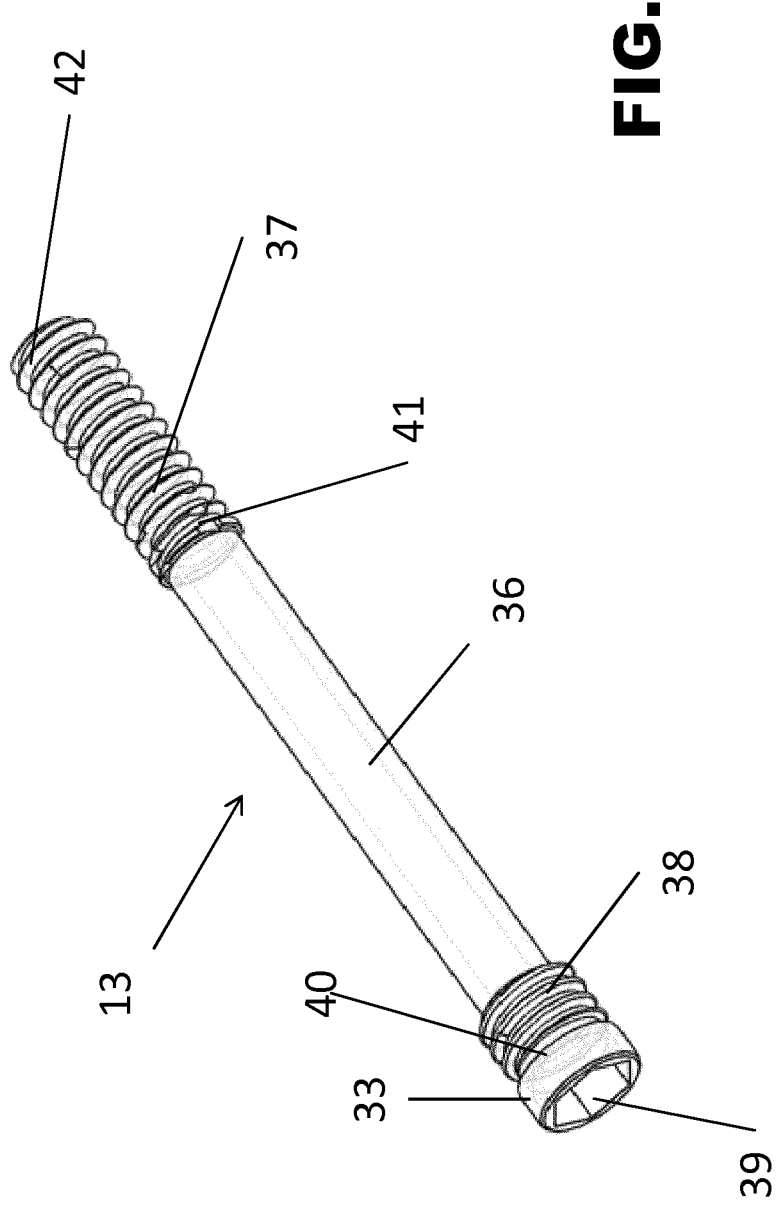
FIG. 9 shows a perspective view of a detail of the inner fixator device according to the invention.
Figure 29:
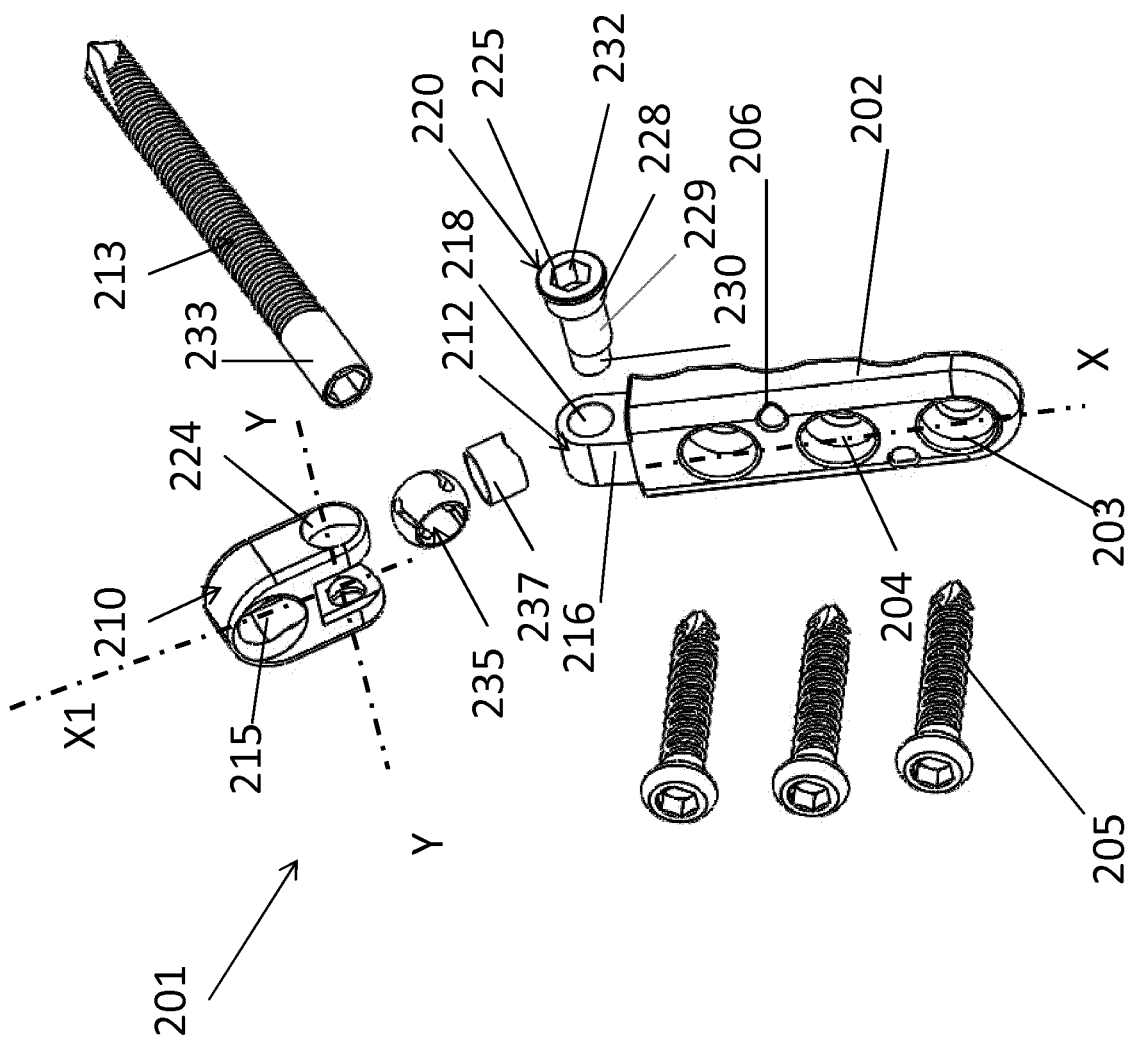
FIG. 29 shows a perspective view of a further alternative embodiment of an inner fixator device according to the present invention in all its components parts.
Figure 32:
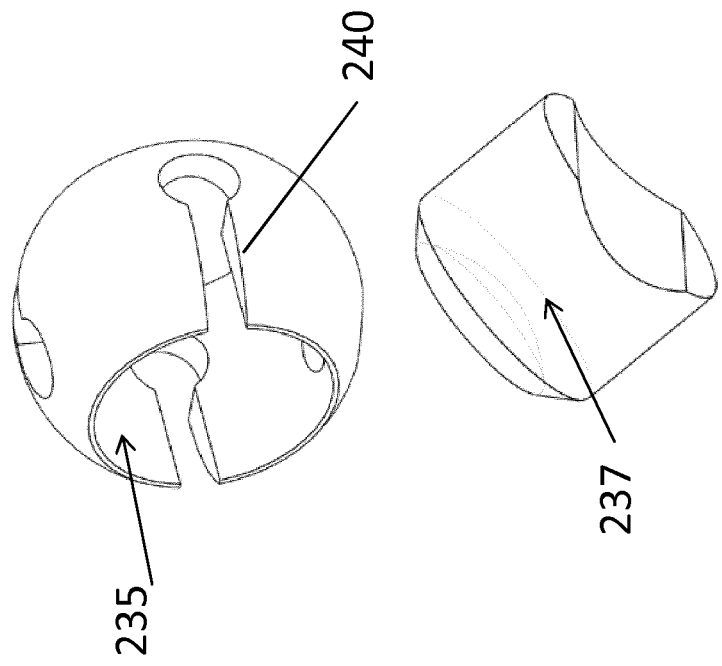
FIG. 32 is a schematic perspective view of another portion of the inner fixator of FIG. 29.

The hinge element 225 is a pin or a nut element with several stages 228, 229, 230, at least the intermediate stage 229 is eccentric with respect to the other two and is inserted and active in said housing seat 222 to block the relative angular positioning of the two plates 202 and 210. Those stages are substantially shown in more detail in FIG. 8 and the embodiment of FIG. 29 implement substantially the same nut element structure.

Each stage 228, 229 and 230 of said pin or nut element 225 is housed in a corresponding portion of the seat 222 represented and defined by the union of a corresponding hole 226, 218 and 224.

Stages 228, 229 and 230 of the pin or nut element 225 have the intermediate stage 229 that is eccentric with respect to the other two and, preferably, with an eccentricity of at least 0.25 mm.

Thanks to this slight eccentricity, a little angular rotation of the nut element 225 in the seat 222 is sufficient to block in situ by interference the relative angle position between the elongated plate 202 and the plate proximal portion 210 according to the needs established by the orthopedic surgeon.

Substantially, the seat 222 and the pin or nut element 225 form locking means 220 which cooperate to fasten the relative angular positioning between the elongated plate 202 and the plate proximal portion 210.

The first stage 228 of the nut element 225 has an hexagonal recess seat 232 for inserting an operating tool, for example an hex wrench.

Therefore, even in this embodiment, the fixator 201 of the invention includes locking means 220 comprising at last a nut element 225 abutting against a portion of the plate proximal portion 10 thus allowing a removeable linking between the elongated plate 202 and the proximal plate 210.

However, in this embodiment the locking means 200 further allow the gripping of the head 233 of the cephalic screw 213 as will be disclosed hereinafter.

Advantageously, in this embodiment the through hole 215 obtained in the plate proximal portion 210 in an almost central position for receiving the cephalic screw 213 is enlarged with respect to the same structure of the first embodiment.

The cephalic screw 213 is preferably cannulated and externally threaded for almost its length. The cephalic screw head 233 is however smooth.

Figure 16:
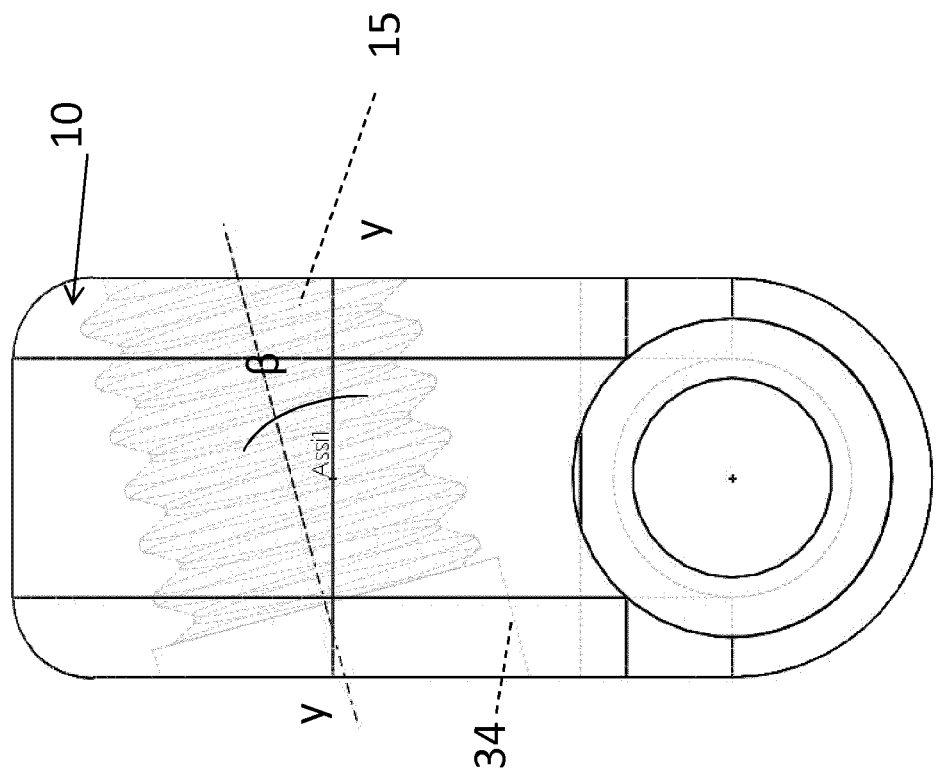
FIGS. 15 and 16 respectively show a partial cross section perspective view and a side view of a component of the inner fixator device according to the invention.

More particularly, the hole 215 obtained through a preferred inclination angle with respect to a transverse axis of the plate proximal portion 210, substantially as shown in FIG. 16. Such inclination eases the correct positioning of the cephalic screw in cooperation with the angulation obtained from the hinge link of the two plate-shaped components 202, 210 of the fixator 201.

Differently from the first embodiment, the hole 215 is not internally threaded since the head 233 of the cephalic screw 213 is smooth. The opening front of the hole 215 presents an enlarged tapered diameter 238 to facilitate the insertion of the cephalic screw 213.

Advantageously, a spherical gripping component 235 has been provided to host the cephalic screw head 233 inside the hole 215 of the proximal plate 210.

This spherical gripping component 235 cooperates with a bushing 237 that is abutting against a side of the spherical component 235 when the locking means 220 are activated. This spherical gripping component 235 may be considered a joint for gripping the head portion 233 of the cephalic screw 213.

This spherical gripping component 235 allows moving angularly the cephalic screw as desired.

This spherical component 235 presents some side partial slots 240 that confer an elastic capability to slightly deform the component 235 itself when pressed.

Figure 31:
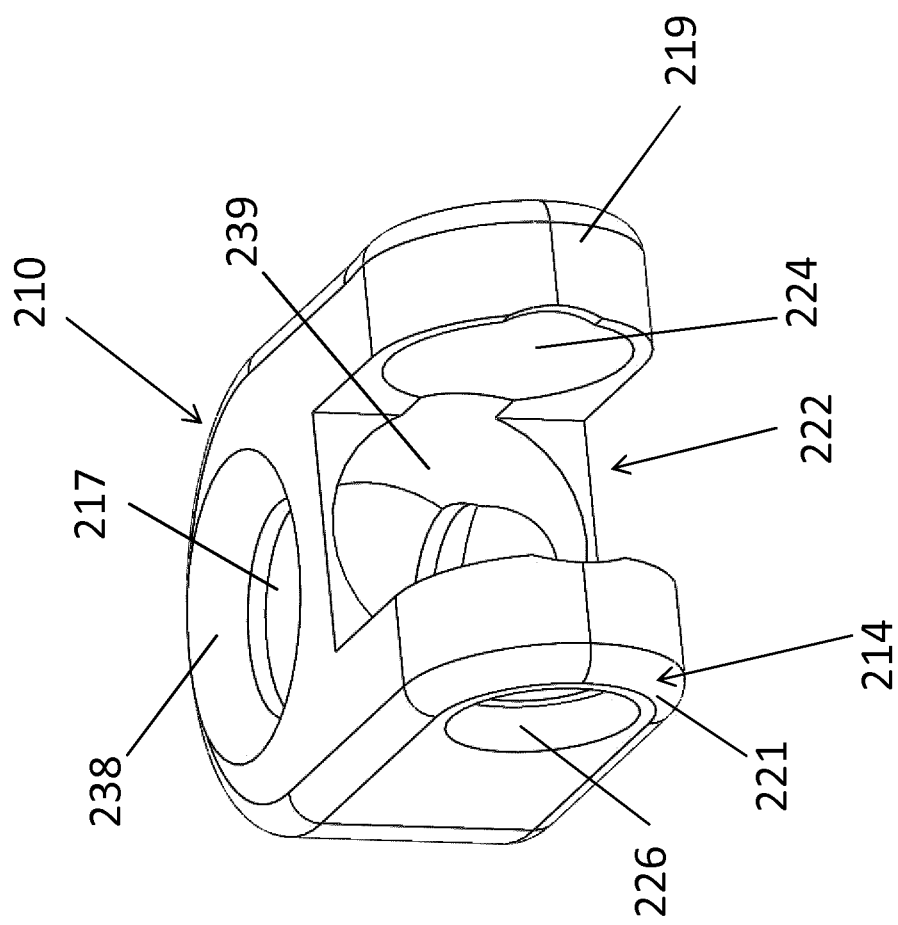
FIG. 31 is a schematic perspective view of the portion of the inner fixator of FIG. 29.

The hole 215 presents an internal partially spherical cavity 217 to host the spherical component 235. This cavity 217 is in communication with an open cylindrical portion 239, visible in FIG. 31, to host the bushing 237.

In other words, the spherical gripping component 235 and the bushing 237 are hosted into corresponding seats 217 and 237 of the proximal plate 210 before the insertion of the cephalic screw 213.

The screw head 233 is gripped by the spherical gripping component 235 when the bushing 237 is pushed against a side of the spherical gripping component 235. This movement of the bushing 217 is forced by the eccentric portion 229 of the nut element 225 activated by the surgeon through the hex wrench inside the recessed seat 232.

When the nut element 225 is turned the eccentric central portion 229 pushes the bushing 237 toward the spherical gripping joint 235. This movement of the nut element 225 also allows a correct positioning and fixing of the proximal plate 210 in abutment against the proximal portion of the great trocanteric bone.

Even this last embodiment of the fixator device of the invention solves the technical problem and provides the same advantaged disclosed with reference to the previous embodiments. Moreover, we may add that in this last example it is even possible to grip and block the position of the cephalic screw with the same action that is necessary to fix the angular positioning between the elongated plate and the proximal plate.

The invention claimed is:

1. An inner plate fixator assembly for correction of severe bone malformations, comprising:
an elongated plate comprising a longitudinal axis, a shaped end, and through holes for receiving bone screws, the shaped end comprising a head with a through hole formed therethrough transverse to the longitudinal axis of the elongated plate;

a plate proximal portion, structurally independent from said elongated plate and hinged to said elongated plate at the shaped end of the elongated plate, the plate proximal portion comprising a longitudinal axis, a pair of stems extending from a lower portion of the plate proximal portion, and at least one through hole for receiving at least one cephalic screw;

a locking system located in proximity of a hinge point between the elongated plate and the plate proximal portion for locking the relative angular positioning of the elongated plate and the plate proximal portion, said locking system comprising a locking pin and a housing seat for receiving said locking pin, wherein said locking pin comprises a proximal portion, a distal portion, and an eccentric central portion each having different diameters, wherein each of the pair of stems of the plate proximal portion are provided with a through hole formed therethrough transverse to the longitudinal axis of the plate proximal portion, wherein the stem through holes align with the through hole of said shaped end head when the plate proximal portion is hinged to the elongated plate to form the housing seat, wherein the stem through holes and the through hole of the shaped end head each have different diameters, and wherein the proximal portion, the distal portion, and the eccentric central portion of said locking pin are correspondingly housed in a respective portion of the housing seat to form a locking hinge linking the elongated plate and the plate proximal portion.

2. The inner plate fixator assembly according to claim 1, wherein said shaped end head is an end projection that extends from the elongated plate at a predetermined inclination angle with respect to the longitudinal axis of the elongated plate, or with respect to a plane where said longitudinal axis lies.

3. The inner plate fixator assembly according to claim 2, wherein said predetermined inclination angle is selected in order to determine a substantially parallel translation of the hinge point of the plate proximal portion with respect to a plane of the elongated plate.

4. The inner plate fixator assembly according to claim 1, wherein said elongated plate further comprises stabilization wire holes located at opposite longitudinal peripheral edges of the elongated plate; wherein a first stabilization wire hole is located closer to a proximal through hole for a bone screw, and wherein a second stabilization wire hole is located on an opposite side of the elongated plate in proximity of an opposite peripheral edge and in a location closer to a distal through hole for a bone screw.

5. The inner plate fixator assembly according to claim 1, further comprising said cephalic screw, wherein said cephalic screw comprises a head having at least a partial thread, a stem and a distal end portion having a thread; the head having a first diameter, the thread of the distal end portion having a second diameter, the stem having a third diameter that is smaller than the first diameter of the head and smaller than the second diameter of the thread of the distal end portion.

6. The inner plate fixator assembly according to claim 5, wherein the thread of the distal end portion of said cephalic screw comprises flat portions formed in threads adjacent to the stem, and configured to prevent a reverse rotation of the cephalic screw when it is installed.

7. The inner plate fixator assembly according to claim 1, further comprising said cephalic screw, wherein said cephalic screw has a smooth head and wherein said plate proximal portion further comprises a spherical gripping element configured to surround and lock said smooth head when said cephalic screw is received in the through hole.

8. The inner plate fixator assembly according to claim 1, wherein the at least one through hole of said plate proximal portion comprises a pair of parallel, internally threaded, through holes configured to receive respective cephalic screws.

9. The inner plate fixator assembly according to claim 1, wherein a lower surface of the elongated plate is shaped with recesses to promote vascularization of tissue adjacent to a bone subjected to surgery.

10. The inner plate fixator assembly according to claim 1, wherein said looking system further comprises a plate element interposed between the head of said shaped end and said plate proximal portion.

* * * * *